US012715915B2

(12) United States Patent
Peterson et al.

(10) Patent No.: US 12,715,915 B2
(45) **Date of Patent: *Aug. 25, 2026**

(54) GOUT FLARE PREVENTION METHODS USING IL-1β BLOCKERS

(71) Applicants: Jeff R. Peterson, Bothell, WA (US); John K. Botson, Anchorage, AK (US)

(72) Inventors: Jeff R. Peterson, Bothell, WA (US); John K. Botson, Anchorage, AK (US)

( * ) Notice: Subject to any disclaimer, the term of this patent is extended or adjusted under 35 U.S.C. 154(b) by 466 days.

This patent is subject to a terminal disclaimer.

(21) Appl. No.: 18/506,701

(22) Filed: Nov. 10, 2023

(65) Prior Publication Data

US 2024/0158490 A1 May 16, 2024

Related U.S. Application Data

(60) Provisional application No. 63/517,598, filed on Aug. 3, 2023, provisional application No. 63/424,621, filed on Nov. 11, 2022.

(51) Int. Cl.

| | |
|---|---|
| ***C07K 16/24*** | (2006.01) |
| ***A61K 31/519*** | (2006.01) |
| ***A61K 38/44*** | (2006.01) |
| ***A61K 39/00*** | (2006.01) |
| ***A61P 19/06*** | (2006.01) |

(52) U.S. Cl.

CPC .......... *C07K 16/245* (2013.01); *A61K 31/519* (2013.01); *A61K 38/44* (2013.01); *A61P 19/06* (2018.01); *A61K 2039/505* (2013.01); *A61K 2039/545* (2013.01)

(58) Field of Classification Search

CPC .................... C07K 16/245; A61K 2039/55527

See application file for complete search history.

(56) References Cited

U.S. PATENT DOCUMENTS

| | | | |
|---|---|---|---|
| 1,141,973 | A | 6/1915 | Nichols |
| 3,451,996 | A | 6/1969 | Sumyk et al. |
| 3,610,795 | A | 10/1971 | Antoine |
| 3,613,231 | A | 10/1971 | Pugh et al. |
| 3,616,231 | A | 10/1971 | Bergmeyer et al. |
| 3,931,399 | A | 1/1976 | Bohn et al. |
| 4,027,676 | A | 6/1977 | Mattei |
| 4,064,010 | A | 12/1977 | Harris et al. |
| 4,141,973 | A | 2/1979 | Balazs |
| 4,169,764 | A | 10/1979 | Takezawa et al. |
| 4,179,337 | A | 12/1979 | Davis et al. |
| 4,251,431 | A | 2/1981 | Carswell et al. |
| 4,297,344 | A | 10/1981 | Schwinn et al. |
| 4,301,153 | A | 11/1981 | Rosenberg |
| 4,312,979 | A | 1/1982 | Takemoto et al. |
| 4,315,852 | A | 2/1982 | Leibowitz et al. |
| 4,317,878 | A | 3/1982 | Nakanishi et al. |
| 4,343,735 | A | 8/1982 | Menge et al. |
| 4,343,736 | A | 8/1982 | Uemura et al. |
| 4,376,110 | A | 3/1983 | David et al. |
| 4,421,650 | A | 12/1983 | Nagasawa et al. |
| 4,425,431 | A | 1/1984 | Takemoto et al. |
| 4,445,745 | A | 5/1984 | Cartesse |
| 4,450,103 | A | 5/1984 | Konrad et al. |
| 4,460,575 | A | 7/1984 | D'Hinterland et al. |
| 4,460,683 | A | 7/1984 | Gloger et al. |
| 4,485,176 | A | 11/1984 | Bollin, Jr. et al. |
| 4,753,796 | A | 6/1988 | Moreno et al. |
| 4,766,106 | A | 8/1988 | Katre et al. |
| 4,797,474 | A | 1/1989 | Patroni et al. |
| 4,816,567 | A | 3/1989 | Cabilly et al. |
| 4,847,079 | A | 7/1989 | Kwan |
| 4,847,325 | A | 7/1989 | Shadle et al. |
| 4,917,888 | A | 4/1990 | Katre et al. |
| 4,945,086 | A | 7/1990 | Benitz et al. |
| 4,946,778 | A | 8/1990 | Ladner et al. |
| 4,966,963 | A | 10/1990 | Patroni |
| 4,987,076 | A | 1/1991 | Takashio et al. |
| 4,992,531 | A | 2/1991 | Patroni et al. |
| 5,008,377 | A | 4/1991 | Patroni et al. |
| 5,010,183 | A | 4/1991 | Macfarlane |
| 5,114,916 | A | 5/1992 | Shirahata et al. |
| 5,122,614 | A | 6/1992 | Zalipsky |
| 5,225,539 | A | 7/1993 | Winter |
| 5,283,317 | A | 2/1994 | Saifer et al. |
| 5,286,637 | A | 2/1994 | Veronese et al. |
| 5,362,641 | A | 11/1994 | Fuks et al. |
| 5,382,518 | A | 1/1995 | Caput et al. |
| 5,428,128 | A | 6/1995 | Mensi-Fattohi et al. |
| 5,458,135 | A | 10/1995 | Patton et al. |
| 5,468,478 | A | 11/1995 | Saifer et al. |
| 5,529,915 | A | 6/1996 | Phillips et al. |

(Continued)

FOREIGN PATENT DOCUMENTS

| | | | |
|---|---|---|---|
| AU | 5251599 | A | 2/2000 |
| CA | 2193993 | A1 | 1/1996 |

(Continued)

OTHER PUBLICATIONS

Abeles, A.M., "PEG-ing down (and preventing?) the cause of pegloticase failure," Arthritis Research & Therapy, Jun. 2014, 16:112., 2 pages.

(Continued)

*Primary Examiner* — Prema M Mertz

(74) *Attorney, Agent, or Firm* — Meunier Carlin & Curfman LLC

(57) ABSTRACT

The present invention discloses methods to prevent gout flares using IL-1β inhibitors. A method of treating gout patients using methotrexate, canakinumab, and pegloticase is described.

27 Claims, 1 Drawing Sheet

Specification includes a Sequence Listing.

(56) References Cited

U.S. PATENT DOCUMENTS

| | | | |
|---|---|---|---|
| 5,541,098 | A | 7/1996 | Caput et al. |
| 5,567,422 | A | 10/1996 | Greenwald |
| 5,585,089 | A | 12/1996 | Queen et al. |
| 5,612,460 | A | 3/1997 | Zalipsky |
| 5,624,903 | A | 4/1997 | Muller et al. |
| 5,633,227 | A | 5/1997 | Muller et al. |
| 5,637,749 | A | 6/1997 | Greenwald |
| 5,643,575 | A | 7/1997 | Martinez et al. |
| 5,653,974 | A | 8/1997 | Hung et al. |
| 5,711,944 | A | 1/1998 | Gilbert et al. |
| 5,762,923 | A | 6/1998 | Gross et al. |
| 5,766,897 | A | 6/1998 | Braxton |
| 5,811,096 | A | 9/1998 | Aleman et al. |
| 5,816,397 | A | 10/1998 | Pratt |
| 5,824,784 | A | 10/1998 | Kinstler et al. |
| 5,880,255 | A | 3/1999 | Delgado et al. |
| 5,919,455 | A | 7/1999 | Greenwald et al. |
| 5,929,231 | A | 7/1999 | Malkki et al. |
| 5,932,462 | A | 8/1999 | Harris et al. |
| 5,948,668 | A | 9/1999 | Hartman et al. |
| 5,955,336 | A | 9/1999 | Shigyo et al. |
| 6,006,753 | A | 12/1999 | Efendic |
| 6,130,318 | A | 10/2000 | Wild et al. |
| 6,201,110 | B1 | 3/2001 | Olsen et al. |
| 6,211,341 | B1 | 4/2001 | Zeelon et al. |
| 6,245,901 | B1 | 6/2001 | Von et al. |
| 6,468,210 | B2 | 10/2002 | Iliff |
| 6,475,143 | B2 | 11/2002 | Iliff |
| 6,524,241 | B2 | 2/2003 | Iliff |
| 6,527,713 | B2 | 3/2003 | Iliff |
| 6,569,093 | B2 | 5/2003 | Iliff |
| 6,575,235 | B2 | 6/2003 | Zupanick et al. |
| 6,576,235 | B1 | 6/2003 | Williams et al. |
| 6,608,892 | B2 | 8/2003 | Shaffer et al. |
| 6,783,965 | B1 | 8/2004 | Sherman et al. |
| 6,913,915 | B2 | 7/2005 | Ensor et al. |
| 7,056,713 | B1 | 6/2006 | Hershfield et al. |
| 7,723,089 | B2 | 5/2010 | Williams et al. |
| 7,811,800 | B2 | 10/2010 | Hartman et al. |
| 7,927,589 | B2 | 4/2011 | Williams et al. |
| 7,927,852 | B2 | 4/2011 | Sherman et al. |
| 7,964,381 | B2 | 6/2011 | Hartman et al. |
| 8,034,594 | B2 | 10/2011 | Hartman et al. |
| 8,067,553 | B2 | 11/2011 | Williams et al. |
| 8,148,123 | B2 | 4/2012 | Hartman et al. |
| 8,178,334 | B2 | 5/2012 | Hartman et al. |
| 8,188,224 | B2 | 5/2012 | Hartman et al. |
| 8,293,228 | B2 | 10/2012 | Hartman et al. |
| 8,465,735 | B2 | 6/2013 | Hartman et al. |
| 8,524,667 | B2 | 9/2013 | Gram et al. |
| 8,541,205 | B2 | 9/2013 | Hartman et al. |
| 8,618,267 | B2 | 12/2013 | Williams et al. |
| 8,913,915 | B2 | 12/2014 | Makino |
| 8,921,064 | B2 | 12/2014 | Sherman et al. |
| 9,017,980 | B2 | 4/2015 | Hartman et al. |
| 9,377,454 | B2 | 6/2016 | Rosario-Jansen et al. |
| 9,402,827 | B2 | 8/2016 | Miner |
| 9,534,013 | B2 | 1/2017 | Fischer et al. |
| 9,670,467 | B2 | 6/2017 | Hartman et al. |
| 9,885,024 | B2 | 2/2018 | Williams et al. |
| 9,926,537 | B2 | 3/2018 | Hartman et al. |
| 9,926,538 | B2 | 3/2018 | Hartman et al. |
| 10,139,399 | B2 | 11/2018 | Rosario-Jansen et al. |
| 10,160,958 | B2 | 12/2018 | Hartman et al. |
| 10,731,139 | B2 | 8/2020 | Hartman et al. |
| 10,823,727 | B2 | 11/2020 | Rosario-Jansen et al. |
| 11,345,899 | B2 | 5/2022 | Hartman et al. |
| 11,598,767 | B2 | 3/2023 | Rosario-Jansen et al. |
| 11,639,927 | B2 | 5/2023 | Rosario-Jansen et al. |
| 2002/0010319 | A1 | 1/2002 | Ansaldi et al. |
| 2002/0151703 | A1 | 10/2002 | Yokoyama et al. |
| 2003/0082786 | A1 | 5/2003 | Ensor et al. |
| 2003/0166249 | A1 | 9/2003 | Williams et al. |
| 2005/0014240 | A1 | 1/2005 | Sherman et al. |
| 2005/0084478 | A1 | 4/2005 | Liu et al. |
| 2006/0188971 | A1 | 8/2006 | Hershfield et al. |
| 2007/0161559 | A1 | 7/2007 | Petrilli et al. |
| 2007/0274977 | A1 | 11/2007 | Hartman et al. |
| 2008/0031864 | A1 | 2/2008 | Williams et al. |
| 2008/0057048 | A1 | 3/2008 | Sherman et al. |
| 2008/0145876 | A1 | 6/2008 | Armstrong et al. |
| 2008/0159976 | A1 | 7/2008 | Hartman et al. |
| 2009/0023715 | A1 | 1/2009 | Brown et al. |
| 2009/0169534 | A1 | 7/2009 | Hartman et al. |
| 2009/0209021 | A1 | 8/2009 | Hartman et al. |
| 2009/0317889 | A1 | 12/2009 | Fischer et al. |
| 2010/0111921 | A1 | 5/2010 | Vicary et al. |
| 2010/0152305 | A1 | 6/2010 | Cedarbaum |
| 2010/0160351 | A1 | 6/2010 | Jenkins et al. |
| 2010/0323422 | A1 | 12/2010 | Williams et al. |
| 2010/0323423 | A1 | 12/2010 | Williams et al. |
| 2011/0104751 | A1 | 5/2011 | Hartman et al. |
| 2011/0217755 | A1 | 9/2011 | Hartman et al. |
| 2011/0287466 | A1 | 11/2011 | Sherman et al. |
| 2012/0070876 | A1 | 3/2012 | Hartman et al. |
| 2012/0149083 | A1 | 6/2012 | Williams et al. |
| 2012/0225046 | A1 | 9/2012 | Hartman et al. |
| 2012/0301454 | A1 | 11/2012 | Rosario-Jansen |
| 2012/0309085 | A1 | 12/2012 | Hartman et al. |
| 2013/0052677 | A1 | 2/2013 | Williams et al. |
| 2013/0084273 | A1 | 4/2013 | Hartman et al. |
| 2013/0330803 | A1 | 12/2013 | Hartman et al. |
| 2014/0363414 | A1 | 12/2014 | Sherman et al. |
| 2015/0197732 | A1 | 7/2015 | Hartman et al. |
| 2016/0035091 | A1 | 2/2016 | Kubassova |
| 2016/0158318 | A1 | 6/2016 | Cohen et al. |
| 2016/0160188 | A1 | 6/2016 | Williams et al. |
| 2016/0377604 | A1 | 12/2016 | Rosario-Jansen et al. |
| 2017/0166873 | A1 | 6/2017 | Fischer et al. |
| 2017/0258927 | A1 | 9/2017 | Johnston |
| 2017/0298326 | A1 | 10/2017 | Hartman et al. |
| 2017/0313993 | A1 | 11/2017 | Hartman et al. |
| 2017/0313994 | A1 | 11/2017 | Hartman et al. |
| 2017/0313995 | A1 | 11/2017 | Hartman et al. |
| 2017/0321193 | A1 | 11/2017 | Hartman et al. |
| 2018/0008665 | A1 | 1/2018 | Qiao |
| 2018/0127432 | A1 | 5/2018 | Trzupek et al. |
| 2018/0188242 | A1 | 7/2018 | Rosario-Jansen et al. |
| 2018/0223263 | A1 | 8/2018 | Sherman et al. |
| 2018/0289776 | A1 | 10/2018 | Johnston |
| 2019/0316097 | A1 | 10/2019 | Hartman et al. |
| 2019/0317083 | A1 | 10/2019 | Rosario-Jansen et al. |
| 2020/0056160 | A1 | 2/2020 | Fischer et al. |
| 2020/0237879 | A1 | 7/2020 | Kent et al. |
| 2020/0237880 | A1 | 7/2020 | Kent et al. |
| 2020/0237881 | A1 | 7/2020 | Kent et al. |
| 2020/0353057 | A1 | 11/2020 | Kent et al. |
| 2021/0079362 | A1 | 3/2021 | Hartman et al. |
| 2021/0181187 | A1 | 6/2021 | Rosario-Jansen et al. |
| 2022/0323445 | A1 | 10/2022 | Peloso et al. |
| 2022/0323550 | A1 | 10/2022 | Peloso |
| 2023/0028134 | A1 | 1/2023 | Rosario-Jansen et al. |
| 2023/0034252 | A1 | 2/2023 | Hartman et al. |
| 2023/0085022 | A1 | 3/2023 | Kent et al. |
| 2023/0173035 | A1 | 6/2023 | Kent et al. |

FOREIGN PATENT DOCUMENTS

| | | | |
|---|---|---|---|
| CN | 1322141 | A | 11/2001 |
| CN | 1322243 | A | 11/2001 |
| CN | 101168052 | A | 4/2008 |
| CN | 101198693 | A | 6/2008 |
| CN | 104066324 | A | 9/2014 |
| DE | 837379 | C | 8/1955 |
| DE | 279486 | A1 | 6/1990 |
| DE | 279489 | A1 | 6/1990 |
| EP | 0028033 | A2 | 5/1981 |
| EP | 0034307 | A2 | 8/1981 |
| EP | 0043980 | A2 | 1/1982 |
| EP | 0055188 | A1 | 6/1982 |
| EP | 0204283 | A2 | 12/1986 |
| EP | 0226448 | A2 | 6/1987 |
| EP | 0279486 | A2 | 8/1988 |
| EP | 0321134 | A2 | 6/1989 |

(56) References Cited

FOREIGN PATENT DOCUMENTS

| | | | |
|---|---|---|---|
| EP | 0408461 | A1 | 1/1991 |
| EP | 0727437 | A2 | 8/1996 |
| EP | 1100542 | A2 | 5/2001 |
| EP | 1100880 | A2 | 5/2001 |
| EP | 2349280 | A1 | 8/2011 |
| JP | S5599189 | A | 7/1980 |
| JP | S55135590 | A | 10/1980 |
| JP | S57192435 | A | 11/1982 |
| JP | S6255079 | A | 3/1987 |
| JP | S62223192 | A | 10/1987 |
| JP | H01216939 | A | 8/1989 |
| JP | H0354581 | A | 3/1991 |
| JP | H03148298 | A | 6/1991 |
| JP | H06255079 | A | 9/1994 |
| JP | H09154581 | A | 6/1997 |
| JP | H10500565 | A | 1/1998 |
| JP | H10502360 | A | 3/1998 |
| JP | H1175876 | A | 3/1999 |
| JP | 3148208 | B2 | 3/2001 |
| JP | 3148298 | B2 | 3/2001 |
| JP | 2002522399 | A | 7/2002 |
| JP | 2002524053 | A | 8/2002 |
| JP | 2003521937 | A | 7/2003 |
| JP | 2005241424 | A | 9/2005 |
| JP | 2008505656 | A | 2/2008 |
| JP | 2008535499 | A | 9/2008 |
| JP | 2008535500 | A | 9/2008 |
| JP | 2013009960 | A | 1/2013 |
| JP | 5599189 | B2 | 10/2014 |
| KR | 19980069019 | A | 10/1998 |
| KR | 0159107 | B1 | 11/1998 |
| KR | 100318706 | B1 | 12/2001 |
| KR | 100333148 | B1 | 12/2002 |
| KR | 100365606 | B1 | 2/2003 |
| KR | 100369838 | B1 | 9/2003 |
| KR | 100488848 | B1 | 5/2005 |
| RU | 2246318 | C2 | 2/2005 |
| RU | 2281954 | C2 | 8/2006 |
| RU | 2290439 | C2 | 12/2006 |
| WO | WO-8604145 | A1 | 7/1986 |
| WO | WO-8700056 | A1 | 1/1987 |
| WO | WO-9216221 | A1 | 10/1992 |
| WO | WO-9419007 | A1 | 9/1994 |
| WO | WO-9419470 | A1 | 9/1994 |
| WO | WO-9423735 | A1 | 10/1994 |
| WO | WO-9423740 | A1 | 10/1994 |
| WO | WO-9511987 | A1 | 5/1995 |
| WO | WO-9525785 | A1 | 9/1995 |
| WO | WO-9601274 | A1 | 1/1996 |
| WO | WO-9623064 | A1 | 8/1996 |
| WO | WO-9808873 | A1 | 3/1998 |
| WO | WO-9831383 | A1 | 7/1998 |
| WO | WO-0007629 | A2 | 2/2000 |
| WO | WO-0008196 | A2 | 2/2000 |
| WO | WO-0008196 | A3 | 3/2000 |
| WO | WO-0159078 | A2 | 8/2001 |
| WO | WO-2002070007 | | 9/2002 |
| WO | WO-03011211 | A2 | 2/2003 |
| WO | WO-03045436 | A1 | 6/2003 |
| WO | WO-2004092393 | A1 | 10/2004 |
| WO | WO-2005110386 | A2 | 11/2005 |
| WO | WO-2006110761 | A2 | 10/2006 |
| WO | WO-2006110819 | A2 | 10/2006 |
| WO | WO-2007100741 | | 9/2007 |
| WO | WO-2008051178 | A2 | 5/2008 |
| WO | WO-2010071865 | A1 | 6/2010 |
| WO | WO-2010151823 | A1 | 12/2010 |
| WO | WO-2010151831 | A1 | 12/2010 |
| WO | WO-2011032175 | A1 | 3/2011 |
| WO | 2012125359 | | 9/2012 |
| WO | WO-2013066353 | A1 | 5/2013 |
| WO | WO-2017156513 | A1 | 9/2017 |
| WO | WO-2018089808 | A1 | 5/2018 |
| WO | WO-2020160322 | A1 | 8/2020 |
| WO | WO-2020160324 | A1 | 8/2020 |
| WO | WO-2020160325 | | 8/2020 |
| WO | WO-2022035828 | A1 | 2/2022 |

OTHER PUBLICATIONS

Abstract Review: "Management of Gout After Pegloticase; Observations of US Clinical Practice from Trio Health and the American Rheumatology Network (ARN)," ACR Convergence, 2020, Abstract ID: 903234, 9 pages.

Abstract Review: "Management of Gout with Pegloticase; Real-World Utilization and Outcomes from Trio Health and the American Rheumatology Network (ARN)," ACR Convergence, 2020, Abstract ID: 903292, 11 pages.

Abuchowski, A. et al., "Effect of Covalent Attachment of Polyethylene Glycol on Immunogenicity and Circulating Life of Bovine Liver Catalase," The Journal of Biological Chemistry, American Society for Biochemistry and Molecular Biology, United States, Jun. 10, 1977, vol. 252, No. 11, pp. 3582-3586.

Abuchowski, A. et al., "Reduction of Plasma Urate Levels in the Cockerel With Polyethylene Glycol-Uricase," The Journal of Pharmacology Experimental Therapeutics, Nov. 1981, vol. 219, No. 2, pp. 352-354.

Abukhalaf et al., "Nonsteroidal Anti-inflammatory Drugs, Disease-Modifying Antirheumatic Drugs, and Agents used in Gout," Handbook of Drug Interactions, Jul. 2011, pp. 415-475.

Acetaminophen Extra Strength-acetaminophen tablet, Physicians Total Care, Inc., Apr. 29, 2016 (Apr. 29, 2016), pp. 1-4. Retrieved from the Internet: https://bit.ly/36wVn98 on Nov. 7, 2020 (Nov. 7, 2020).

Adams, P., et al., "Current Estimates From the National Health Interview Survey, 1996," Vital Health Study, Oct. 1999, Series 10, No. 200, 212 Pages.

"Aggregate", Stedman's Medical Dictionary 27th Edition, PDR Electronic Library, Accessed on Jun. 10, 2009, 1 Page, Retrieved from URL: http://www.thomsonhe.com/pdrel/librarian/ND.

Akkemik et al., "Effects of some drugs on human erythrocyte glucose 6-phosphate dehydrogenase: an in vitro study," Journal of Enzyme Inhibition and Medicinal Chemistry, 25(6), Dec. 2010, pp. 871-875.

Alamillo J.M., et al., "Purification and Molecular Properties of Urate Oxidase From Chlamydomonas Reinhardtii," Biochimica et Biophysica Acta, Elsevier Science Publishers B.V., Netherlands, Jan. 29, 1991, vol. 1076, pp. 203-208.

Albert et al., Increased Efficacy and Tolerability of Pegloticase in Patients With Uncontrolled Gout Co-Treated With Methotrexate: A Retrospective Study. Rheumatol Ther. Jul. 27, 2020, vol. 7, pp. 639-648.

Al-Shawi A., et al., "A Novel Immunoradiometric Assay for Human Liver Ferritin," Journal of Clinical Pathology, Apr. 1983, vol. 36, No. 4, pp. 440-444, Abstract only.

Altschul, S. F., et al., "Gapped BLAST and PSI-BLAST: a new generation of protein database search programs", Nucleic Acids Research (Sep. 1, 1997); 25(17): 3389-3402.

Altschul, S.F., et al., "Basic local alignment search tool," J. Mol. Biol. 215:403-410 (Oct. 5, 1990).

Alvares K., et al., "Rat Urate Oxidase Produced by Recombinant Baculovirus Expression: Formation of Peroxisome Crystalloid Core-like Structures," Cell Biology, Proceedings of the National Academy of Sciences of the USA, Jun. 1992, vol. 89, pp. 4908-4912.

Alvares K., et al., "The Nucleotide Sequence of a Full Length cDNA Clone Encoding Rat Liver Urate Oxidase," Biochemical and Biophysical Research Communications, Academic Press, Inc., United States, Feb. 15, 1989, vol. 158, No. 3, pp. 991-995.

Alvarez-Hernandez et al., "Validation of the health assessment questionnaire disability index in patients with gout," Arthritis & Rheumatism, May 2008, vol. 59, No. 5, pp. 665-669.

Alvarez-Lario et al., "Uric acid and evolution," Rheumatology, Jul. 2010, 49, pp. 2010-2015.

"Amino Acid Sequence of Amino Truncated Chimeric Pig-Baboon Uricase," May 30, 2000, Retrieved from EBI Accession No. GSP: AAY69153, 2 Pages, XP002404207.

(56) References Cited

OTHER PUBLICATIONS

Antonopoulos C.A., et al., "The Precipitation of Polyanions by Long-Chain Aliphatic Ammonium Compounds," Biochimica et Biophysica Acta, Dec. 9, 1961, vol. 54, pp. 213-226.
Arellano et al., "Allopurinol hypersensitivity syndrome: a review," Mar. 1993, 27(3), pp. 337-343.
Asci et al., "The impact of gallic acid on the methotrexate-induced kidney damage in rats," Journal of Food and Drug Analysis, vol. 25, Issue 4, Oct. 2017, pp. 890-897.
Assadi F., "Managing New Onset Gout in Pediatric Renal Transplant Recipients: when, how, to what extent," Journal of Nephrology, Jul.-Aug. 2013, 26(4), pp. 624-628 2013.
Augustsson J., et al., "Low-Dose Glucocorticoid Therapy Decreases Risk for Treatment-Limiting Infusion Reaction to Infliximab in Patients with Rheumatoid Arthritis," Extended Report, Annals of the Rheumatic Diseases, Nov. 2007, vol. 66, pp. 1462-1466.
Baert et al., "Influence of Immunogenicity on the Long-Term Efficay of Infliximab in Crohn's Disease," The New England Journal of Medicine 348, No. 7, Feb. 2003, pp. 601-608.
Baraf et al., "Infusion-related reactions with pegloticase, a recombinant uricase for the treatment of chronic gout refractory to conventional therapy," Journal of Clinical Rheumatology, Dec. 2014, 20(8):427-432.
Baraf H.S.B., et al., "Resolution of Tophi With Intravenous Peguricase in Refractory Gout," Arthritis & Rheumatism, Sep. 2005 Supplement, vol. 52, No. 9, p. S105.
Baraf H.S.B., et al., "Resolution of Tophi With Intravenous Peguricase in Refractory Gout," Presented at American College of Rheumatology, Annual Scientific Meeting, San Diego, CA, Poster 194, Nov. 13-17, 2005, 1 Page.
Baraf H.S.B., et al., "Resolution of Tophi With Intravenous Peguricase in Treatment-Failure Gout," Presented at the EULAR—Annual European Congress of Rheumatology, Amsterdam, Netherlands, Poster 465, Annals of the Rheumatic Diseases, Jun. 21-24, 2006, vol. 65, Supplement 2: 256, 1 Page.
Baraf H.S.B., et al., "Tophus Burden Reduction With Pegloticase: Results From Phase 3 Randomized Trials and Open-Label Extension in Patients With Chronic Gout Refractory to Conventional Therapy," Arthritis Research & Therapy, Sep. 26, 2013, vol. 15, No. 5:R137, 11 Pages.
Bastos et al., "Methotrexate: Studies on cellular metabolism. IV. Effect on the mitochondrial oxidation of cytosolic-reducing equivalents in HeLa cells," Cell Biochemistry & Function, Oct. 1990, vol. 8, Issue 4, pp. 199-203.
Bayat S., et al., "Development of a Dual-Energy Computed Tomography Scoring System for Measurement of Urate Deposition in Gout," Arthritis Care & Research, Jun. 2016, vol. 68, No. 6, pp. 769-775.
Becker M., et al., "Activation of Hydroxylic Polymers—by Reaction with Carbonate or Chloroformate Ester in Presence of Amine," English Abstract, Derwent World Patents Index, Accession No. 8448552, 2004, 1 Page.
Becker M.A., et al., "Febuxocat Compared with Allopurinol in Patients with Hyperuricemia and Gout," The New England Journal of Medicine, Dec. 8, 2005, vol. 353, No. 23, pp. 2450-2461.
Becker M.A., "Hyperuricemia and Gout," The Metabolic and Molecular Bases of Inherited Disease, Edited by Scriver C.R, Beaudet A.L, Sly W.S, Valle D, 8th Edition, New York, McGraw-Hill, 2001, vol. 11, pp. 2513-2535.
Benbacer L., et al., "Interspecies Aminopeptidase-n Chimeras Reveal Species-specific Receptor Recognition by Canine Coronavirus, Feline Infectious Peritonitis Virus, and Transmissible Gastroenteritis Virus," Journal of Virology, Jan. 1997, vol. 71, No. 1, pp. 734-737, JPN6014045520.
Ben-Bassat A., et al., "Amino-Terminal Processing of Proteins," Nature, Mar. 19, 1987, vol. 326, 1 Page.
Ben-Bassat A., et al., "Processing of the Initiation Methionine From Proteins: Properties of the *Escherichia coli* Methionine Aminopeptidase and Its Gene Structure," Journal of Bacteriology, Feb. 1987, vol. 169, No. 2, pp. 751-757.
Ben-Horin et al., "Addition of an Immunomodulator to Infliximab Therapy Eliminates Antidrug Antibodies in Serum and Restores Clinical Response of Patients with Inflammatory Bowel Disease," Clinical Gastroenterology and Hepatology, vol. 11, Issue 4, Apr. 2013, pp. 444-447.
Berendsen H.J.C., "A Glimpse of the Holy Grail?," Science, Oct. 23, 1998, vol. 282, pp. 642-643.
Berhanu A., et al., "Pegloticase Failure and a Possible Solution: Immunosuppression to Prevent Intolerance and Inefficacy in Patients with Gout," Seminars in Arthritis and Rheumatism, 2017, vol. 46, No. 6, pp. 754-758.
Bessen et al., "Concomitant immunosuppressant use with pegloticase in patients with tophaceous gout—a case series," International Journal of Clinical Rheumatology 2019;14(6):238-245.
Bessen et al., "Recapture and improved outcome of pegloticase response with methotrexate—A report of two cases and review of the literature," Seminars in Arthritis and Rheumatism, Accepted Manuscript, (2018), 12 pages.
Bessen et al., "Recapture and improved outcome of pegloticase response with methotrexate—A report of two cases and review of the literature," Seminars in Arthritis and Rheumatism, Aug. 2019, vol. 49, No. 1, pp. 56-61.
Biggers et al., "Pegloticase, a polyethylene glycol conjugate of uricase for the potential intravenous treatment of gout," Current Opinion in Investigational Drugs (London, England: 2000), vol. 9, Issue 4, Apr. 1, 2008, pp. 422-429.
Bird, R. E., et al., "Single-chain antigen-binding proteins", Science (1988); 242 (4877): 423-426.
Blumberg B.S., et al., "Further Evidence on the Protein Complexes of Some Hyauronic Acids," Biochemical Journal, Jan. 1958, vol. 68, pp. 183-188.
Bossavy J.P., et al., "Comparison of the Antithrombotic Effect of PEG-Hirudin and Heparin in a Human Ex Vivo Model of Arterial Thrombosis," Arteriosclerosis, Thrombosis and Vascular Biology, Journal of the American Heart Association, United States, May 1999, vol. 19, pp. 1348-1353.
Botson et al., "Pegloticase in combination with methotrexate in patients with uncontrolled gout: A multicenter, open-label study (MIRROR)," The Journal of Rheumatology, May 2021;48:767-774, doi: 10.3899/jrheum.200460.
Botson et al., "Pretreatment and Coadministration with Methotrexate Improved Durability of Pegloticase (Krystexxa) Response: A Prospective, Proof-of-Concept, Case Series," Abstract, Arthritis Rheumatology, 2018; 70 (suppl 10), https://acrabstracts.org/abstract/pretreatment-andcoadministration-with-methotrexate-improved-durability-of-pegloticase-krystexxa-response-aprospective-proof-of-concept-case-series/, Accessed Sep. 11, 2018, 2 pages.
Botson et al., "Pretreatment and co-administration with methotrexate improved durability of pegloticase response: a prospective observational, proof-of-concept, case series [Abstract]," SAT0404 Annals of the Rheumatic Diseases, Jun. 2019, vol. 78, Issue Suppl. 2, A1289-A1290.
Botson et al., "Pretreatment and Co-Administration with Methotrexate Improved Durability of Pegloticase Response: A Prospective, Observational, Proof-of-Concept, Case Series," Poster presented at the 2018 Annual Scientific Meeting of the American College of Rheumatology, Oct. 19-24, 2018, 1 page.
Botson et al., "Pretreatment and co-administration with methotrexate improved durability of pegloticase response," Journal of Clinical Rheumatology, vol. 28, No. 1, Jan. 2022, e129-e134, doi: 10.1097/RHU.0000000000001639.
Bradley C.M., et al., "Limits of Cooperativity in a Structurally Modular Protein: Response of the Notch Ankyrin Domain to Analogous Alanine Substitutions in Each Repeat," Journal of Molecular Biology, Nov. 22, 2002, vol. 324, pp. 373-386.
Braun A., et al., "Development and Use of Enzyme-Linked Immunosorbent Assays (ELISA) for the Detection of Protein Aggregates in Interferon-Alpha (IFN-.alpha) Formulations," Pharmaceutical Research, Plenum Publishing Corporation, United States, Oct. 1997, vol. 14, No. 10, pp. 1394-1400.
Braun A., et al., "Protein Aggregates Seem to Play a Key Role Among the Parameters Influencing the Antigenicity of Interferon Alpha (IFN-.alpha.) in Normal and Transgenic Mice," Pharmaceu-

(56) References Cited

OTHER PUBLICATIONS tical Research, Plenum Publishing Corporation, United States, Oct. 1997, vol. 14, No. 10, pp. 1472-1478.
Brenda Enzyme Database: "E.C. 1.7.3.3, Urate Oxidase," 42 Pages, [Retrieved on Mar. 27, 2008] Retrieved from URL: www.brenda-enzymes.info.
Bringham, M. D. et al., "Immunosuppressant Use and Gout in the Prevalent Solid Organ Transplantation Population," J of the American Society of Nephrology, Progress in Transplantation, Jun. 2020, 30(2), pp. 103-110.
Broadwell et al., "Community Practice Experiences with a Variety of Immunomodulatory Agents Co-Administered with Pegloticase for the Treatment of Uncontrolled Gout," Rheumatology and Therapy, Dec. 2022, 9(6), pp. 1549-1558.
Buch M.H., et al., "Shortening Infusion Times for Infliximab Administration," Rheumatology, Apr. 2006, vol. 45, pp. 485-486.
Burnham N.L., "Polymers for Delivering Peptides and Proteins," American Journal of Hospital Pharmacy, American Society of Hospital Pharmacists, Inc., United States, Jan. 15, 1994, vol. 51, pp. 210-218.
Caetano et al., "Effect of methotrexate (MTX) on NAD(P)+ dehydrogenases of HeLa cells malic enzyme, 2-oxoglutarate and isocitrate dehydrogenases," Cell Biochemistry & Function, Dec. 1997, vol. 15, Issue 4, pp. 259-264.
Calabrese L.H., et al., "Frequency, Distribution and Immunologic Nature of Infusion Reactions in Subjects Receiving Pegloticase for Chronic Refractory Gout," Arthritis Research & Therapy, Dec. 2017, vol. 19, No. 1:19, 1-7 Pages.
Caliceti P., et al., "Biopharmaceutical Properties of Uricase Conjugated to Neutral and Amphiphilic Polymers," Bioconjugate Chemistry, American Chemical Society, Jun. 2, 1999, vol. 10, No. 4, pp. 638-646.
Carter W.A., "Interferon: Evidence for Subunit Structure," Proceedings of the National Academy of Sciences of the United States of America, Oct. 1970, vol. 67, No. 2, pp. 620-628.
Chen et al., "Contemporary Prevalence of Gout and Hyperuricemia in the United States and Decadal Trends: The National Health and Nutrition Examination Survey 2007-2016," Arthritis Rheumatology, Jun. 2019; 71(6), pp. 991-999.
Chen R.H.-L., et al., "Properties of Two Urate Oxidases Modified by the Covalent Attachment of Poly(Ethylene Glycol)," Biochimica et Biophysica Acta (BBA)—Enzymology, Aug. 13, 1981, vol. 660, pp. 293-298.
Choe et al., "Association between serum uric acid and inflammation in rheumatoid arthritis: Perspective on lowering serum uric acid of leflunomide," Clinica Chimica acta, vol. 438, Jan. 1, 2015, pp. 29-34, https://doi.org/10.1016/j.cca.2014.07.039.
Chua C.C., et al., "Use of Polyethylene Glycol-Modified Uricase (PEG-Uricase) to Treat Hyperuricemia in a Patient with Non-Hodgkin Lymphoma," Annals of Internal Medicine, American College of Physicians, United States, Jul. 15, 1988, vol. 109, pp. 114-117.
Cipolleta E., et al., "Association between gout flare and subsequent cardiovascular events among patients with gout," JAMA, Aug. 2022, 328(5), pp. 440-450.
Cipolleta, E., et al., "Risk of venous thromboembolism with gout flares," Arthritis & Rheumatology, Feb. 2023, 30 pages.
Clark R., et al., "Long-acting Growth Hormone Produced by Conjugation with Polyethylene Glycol," Journal of Biological Chemistry, Sep. 6, 1996, vol. 271, No. 36, pp. 21969-21977.
ClinicalTrials.gov Identifier NCT02598596 (Year: 2015), 14 pages.
ClinicalTrials.gov Identifier NCT03303989 (Year: 2017), 30 pages.
Clive, D. M. "Renal Transplant-Associated Hyperuricemia and Gout," Journal of the American Society of Nephrology, May 1, 2000 (May 1, 2000), vol. 11, No. 5, pp. 974-979.
Coiffier et al., "Efficacy and safety of rasburicase (recombinant urate oxidase) for the prevention and treatment of hyperuricemia during induction chemotherapy of aggressive non-hodgkin's lymphoma: Results of the GRAAL1 (Groupe d'Etude des lymphomes de l'adulte trial on rasburicase activity in adult lymphoma) study," Journal of Clinical Oncology, vol. 21, No. 23, Dec. 2003, pp. 4402-4406.
Cole, S. et al. "The EBV-Hybridoma Technique and Its Application to Human Lung Cancer," Monoclonal Antibodies and Cancer Therapy Jan. 27, 1985, pp. 77-96.
Cole-Showers et al., "Effects of proanthocyanidin and methotrexate on glucose-6-phosphate dehydrogenase (G6PD) and glutathione reductase (GR) in an animal model," Journal of Food Agriculture and Environment, vol. 10, Issue 1, Jan. 2012, pp. 231-234.
Colloc'H N., et al., "Crystal Structure of the Protein Drug Urate Oxidase-Inhibitor Complex at 2.05 ANG. Resolution," Nature Structural Biology, Nature Publishing Group, Nov. 1997, vol. 4, No. 11, pp. 947-952.
Conley T.G., et al., "Thermodynamics and Stoicheiometry of the Binding of Substrate Analogues to Uricase," Biochemical Journal, The Biochemical Society, United Kingdom, Jun. 1, 1980, vol. 187, pp. 727-732.
Cooper J.F., "Resolving LAL Test Interferences," Journal of Parenteral Science and Technology, Jan.-Feb. 1990, vol. 44, No. 1, pp. 13-15.
Cote, R. et al., "Generation of human monoclonal antibodies reactive with cellular antigens," Proceedings of the National Academy of Sciences, Apr. 1983, vol. 80, pp. 2026-2030.
Cotton et al., "Glucose-6-Phosphate Dehydrogenase in the Blood of Psoriatics, and the Effects of Methotrexate," Dermatology, 1973, vol. 147, No. 6, pp. 399-405.
Crews et al., "Effect of Allopurinol Versus Urate Oxidase on Methotrexate Pharmacokinetics in Children with Newly Diagnosed Acute Lymphoblastic Leukemia," Cancer, Jan. 2010, pp. 227-232.
Crivelli E., et al., "A Single Step Method for the Solubilization and Refolding of Recombinant Protein from *E. coli* Inclusion Bodies," Australian Journal of Biotechnology, Apr. 1991, vol. 5, No. 2, pp. 78-80, 86.
Dady et al., "Methotrexate with thymidine, inosine, and allopurinol rescue: a phase I clinical study," Cancer Treatment Report 65, Jan. 1, 1981, pp. 37-43.
Davis F.F., et al., "Enzyme-Polyethylene Glycol Adducts: Modified Enzymes with Unique Properties," In Enzyme Engineering, Edited by Broun G.B., et al., Plenum Press, New York, 1978, vol. 4, pp. 169-173.
Davis S., et al., "Hypouricaemic Effect of Polyethyleneglycol Modified Urate Oxidase," The Lancet, London, GB, Aug. 8, 1981, pp. 281-283, XP000577404.
Dean et al., "Pegloticase Therapy and G6PD Genotype," National Center of Biotechnology Information, Oct. 2020, pp. 1-10.
Delgado et al., "The uses and properties of PEG-linked proteins". Critical Reviews in Therapeutic Drug Carrier Systems (Jan. 1, 1992); 9(3-4): 249-304.
Derynck R., et al., "Expression of Human Fibroblast Interferon Gene in *Escherichia coli*," Nature, Sep. 18, 1980, vol. 287, pp. 193-197.
Donadio, D., et al., "Anaphylaxis-like Manifestations After Intravenous Injection of Urate Oxidase in an Asthmatic Child With Acute Leukemia," La Nouvelle Presse Medicale, 1981, vol. 10, pp. 711-712. (1 page English Translation).
Doyle et al., "Treatment with Infliximab plus Methotrexate Improves Anemia in Patients with Rheumatoid Arthritis Independent of Improvement in Other Clinical Outcome Measures—A Pooled Analysis from Three Large, Multicenter, Doubled-Blind, Randomized Clinical Trials," Seminars in Arthritis and Rheumatism, vol. 39, Issue 2, Oct. 2009, pp. 123-131.
Ducourau et al., "Methotrexate effect on immunogenicity and long-term maintenance of adalimumab in axial spondyloarthritis: a multicentric randomised trial," Rheumatic & Musculoskeletal Diseases Open, Jan. 2020, 6:e001047, pp. 1-9.
"EC 1.7.3.3, urate oxidase," BRENDA Enzyme Database, available via internet at www.brenda.uni-koeln.de/, 25 pages.
Embery, G., "Glycosaminoglycans of Human Dental Pulp," Journal de Biologie Buccale, Sep. 1976, vol. 4, pp. 229-236.
Emmerson, B.T., "The Management of Gout," The New England Journal of Medicine, Feb. 15, 1996, vol. 334, No. 7, pp. 445-451.

(56) References Cited

OTHER PUBLICATIONS

Estimated Glomerular Filtration Rate (eGFR), Kidney Health Australia, May 31, 2017, (Apr. 31, 2017), pp. 1-3. Retrieved from the Internet: https://kidney.org.au/uploads/resources/egfr-fact-sheet.pdf on Nov. 7, 2020 (Nov. 7, 2020).
"ExPasy ProtParam Tool," pp. 1-2, [Retrieved on Dec. 19, 2018], Retrieved from the Internet: URL: https://web.expasy.org/cgi-bin/protparam/protparam.
Fam, A.G., "Strategies and Controversies in the Treatment of Gout and Hyperuricaemia," Bailliere's Clinical Rheumatology: International Practice and Research, Elsevier Science Ltd., Aug. 1990, vol. 4, No. 2, pp. 177-192.
FDA—Drug Safety Brouchure—Ref ID 3116893, Published on the Web for Krystexxa, Apr. 2012, pp. 1-14, Retrieved from URL: http://www.accessdata.fda.gov/drugsatfda_docs/label/2012/125293s034lbl.pdf.
"FDA Approves Krystexxa® (pegloticase) Injection Co-Administered with Methotrexate, Expanding the Labeling to Help More People with Uncontrolled Gout Achieve a Complete Response to Therapy," Benzinga, Business Wire Press Releases, Jul. 8, 2022, 4 pages.
"FDA Approves Krystexxa® (pegloticase) Injection Co-Administered with Methotrexate, Expanding the Labeling to Help More People with Uncontrolled Gout Achieve a Complete Response to Therapy," BioSpace, Jul. 8, 2022, 5 pages.
"FDA Approves Krystexxa® (pegloticase) Injection Co-Administered with Methotrexate, Expanding the Labeling to Help More People with Uncontrolled Gout Achieve a Complete Response to Therapy," StreetInsider, Business Wire, Press Releases, Jul. 8, 2022, 3 pages.
"FDA Approves Krystexxa® (pegloticase) Injection Co-Administered with Methotrexate, Expanding the Labeling to Help More People with Uncontrolled Gout Achieve a Complete Response to Therapy," Yahoo!Finance, Business Wire, Press Releases, Jul. 8, 2022, 4 pages.
"FDA Approves Peglioticase Injection Plus Methotrexate for Patients with Uncontrolled Gout," Rheumatology Network, Jul. 8, 2022, 1 page.
"FDA approves peglioticase, methotrexate combo in patients with uncontrolled gout," Healio Rheumatology, Jul. 8, 2022, 2 pages.
"FDA Approves Peglioticase Plus Methotrexate for Uncontrolled Gout," HCPLive, Jul. 8, 2022, 1 page.
"FDA approves pegloticase injection coadministered with methotrexate for gout," AJMC, Jul. 8, 2022, 2 pages.
"FDA decisions to watch in rheumatology in Second Half of 2022," Rheumatology Network, Jun. 29, 2022, 3 pages.
Feagan et al., "Methotrexate in combination with infliximab is no more effectve than infliximab alone in patients with crohn's disease," Gastroenterology, Mar. 2014, 146(3), pp. 681-688.
Flinta, C., et al., "Sequence Determinants of Cytosolic N-Terminal Protein Processing," European Journal of Biochemistry, Jan. 2, 1986, vol. 154, No. 1, pp. 193-196.
Forrest A., et al., "A New Approach for Designing Population Sparse Sampling Strategies—Applied to Ciprofloxacin PKS," Abstracts of Papers, Feb. 1991, vol. 49, No. 2, p. 153.
Francis, G., et al., "PEGylation of Cytokines and other Therapeutic Proteins and Peptides: the Importance of Biological Optimisation of Coupling Techniques," International Journal of Hematology, Jul. 1998, vol. 68, pp. 1-18, 19 pages.
Fridovich I., "The Competitive Inhibition of Uricase by Oxonate and by Related Derivatives of s-Triazines," The Journal of Biological Chemistry, Jun. 1965, vol. 240, No. 6, pp. 2491-2494.
Friedman T., et al., "The Urate Oxidase Gene of *Drosophila pseudoobscura* and *Drosophila melanogaster*: Evolutionary Changes of Sequence and Regulation," Journal of Molecular Evolution, Jan. 1992, vol. 34, No. 1, pp. 62-77, Abstract only.
Fuertges F., et al., "The Clinical Efficacy of Poly (Ethylene Glycol)-Modified Proteins," Journal of Controlled Release, Elsevier Science, The Netherlands, Jan. 1990, vol. 11, pp. 139-148.
Fujita T., et al., "Tissue Distribution of In-Labeled Uricase Conjugated with Charged Dextrans and Polyethylene Glycol," Journal of Pharmacobio-Dynamics, Pharmaceutical Society of Japan, Nov. 1991, vol. 14, pp. 623-629.
Gaertner H.F., et al., "Site-Specific Attachment of Functionalized Poly(ethylene glycol) to the Amino Terminus of Proteins," Bioconjugate Chemistry, American Chemical Society, United States, Jan. 30, 1996, vol. 7, No. 1, pp. 38-44.
Gaffo et al., "Developing a provisional definition of flare in patients with established gout," May 2012, 64(5), pp. 1508-1517, https://pubmed.ncbi.nlm.nih.gov/22083456/.
Ganson N.J., et al., "Antibodies to Polyethylene Glycol (PEG) during Phase I Investigation of PEG-Urate Oxidase (PEG-uricase; Puricase.RTM.) for Refractory Gout," Presented at American College of Rheumatology Annual Scientific Meeting at San Antonio, TX, Oct. 16-21, 2004, Poster 808, 7 Pages.
Ganson N.J., et al., "Control of Hyperuricemia in Subjects with Refractory Gout, and Induction of Antibody against Poly(ethylene Glycol) (PEG), in a Phase I Trial of Subcutaneous PEGylated Urate Oxidase," Arthritis Research and Therapy, 2005, vol. 8, No. 1 : (R12), pp. 1-10.
Garay et al., "Antibodies against polyethylene glycol in healthy subjects and in patients treated with PEG-conjugated agents," Expert Opinion on Drug Delivery, Nov. 2012, 9(11), pp. 1319-1323.
Giglione C., et al., "Control of Protein Life-span by N-terminal Methionine Excision," The EMBO—European Molecular Biology Organization Journal, Jan. 2, 2003, vol. 22, No. 1, pp. 13-23.
Goeddel D.V., et al., "Human Leukocyte Interferon Produced by *E. coli* Is Biologically Active," Nature, Oct. 2, 1980, vol. 287, 6 Pages.
Goldman S.C., et al., "A Randomized Comparison Between Rasburicase and Allopurinol in Children with Lymphoma or Leukemia at High Risk for Tumor Lysis," Blood, May 15, 2001, vol. 97, No. 10, pp. 2998-3303.
Goss et al., "Methotrexate Dose in Patients With Early Rheumatoid Arthritis Impacts Methotrexate Polyglutamate Pharmacokinetics, Adalimumab Pharmacokinetics, and Efficacy: Pharmacokinetic and Exposure-response Analysis of the CONCERTO Trial," Clinical Therapeutics, vol. 40, Issue 2, Feb. 2018, pp. 309-319.
Greenberg M.L., et al., "A Radiochemical-High-Performance Liquid Chromatographic Assay for Urate Oxidase in Human Plasma," Analytical Biochemistry, Academic Press, Inc., United States, Feb. 1, 1989, vol. 176, pp. 290-293.
"Guidance for Industry: Immunogenicity Assessment for Therapeutic Protein Products," U.S. Department of Health and Human Services Food and Drug Administration, Aug. 2014, 39 pages.
Guttmann A., et al., "Pegloticase in Gout Treatment—Safety Issues, Latest Evidence and Clinical Considerations," Therapeutic Advances in Drug Safety, Dec. 2017, vol. 8, No. 12, pp. 379-388.
Hamburger, S., et al., "Arthritis Advisory Committee Meeting, Pegloticase (Krystexxa) IV fusion," dated Jun. 16, 2009, pp. 1-155, [Retrieved on Aug. 4, 2010], Available on the internet:< url: http=""www.fda.gov/downloads/AdvisoryCommittees/CommitteesMeetingMaterials/DrugsAdvisoryCommittee/UCM167777.pdf, Especially, pp. 108-115.</url:>.
Hande K.R., et al., "Severe Allopurinol Toxicity. Description and Guidelines for Prevention in Patients in Renal Insufficiency," The American Journal of Medicine, Excerpta Medica, United States, Jan. 1984, vol. 76, pp. 47-56.
Harris J.M., et al., "Effect of Pegylation on Pharmaceuticals," Nature Reviews Drug Discovery, Mar. 2003, vol. 2, No. 3, pp. 214-221.
Hartmann G., "Exchange In Vitro of Subunits between Enzymes from Different Organisms: Chimeras of Enzymes," Angewandte Chemie International edition in English, Apr. 1976, vol. 15, No. 4, pp. 181-186, JPN6014045522.
Hascall V., et al., "Aggregation of Cartilage Proteoglycans," Journal of Biological Chemistry, Jul. 10, 1974, vol. 249, No. 13, pp. 4232-4241, pp. 4242-4249, and pp. 4250-4256.
Hazen J., "Adjuvants—Terminology, Classification, and Chemistry," Weed Technology, Oct. 2000, vol. 14, pp. 773-784.

(56) References Cited

OTHER PUBLICATIONS

Hedlund L., et al., "Magnetic Resonance Microscopy of Toxic Renal Injury by Bromoethylamine in Rats," Fundamental and Applied Toxicology, Academic Press, May 1991, vol. 16, pp. 787-797.
Heftmann E., et al., "Chromatography: Fundamentals and Applications of Chromatographic and Electrophoretic Methods. Part A: Fundamentals and Techniques," Journal of Chromatography, 1983, vol. 22A, pp. A104-A110.
Heinegard D., et al., "Characterization of Chondroitin Sulfate Isolated from Trypsin-Chymotrypsin Digests of Cartilage Proteoglycans," Archives of Biochemistry and Biophysics, Nov. 1974, vol. 165, No. 1, pp. 427-441.
Henney C., et al., "Antibody Production to Aggregated Human gamma.G-Globulin in Acquired Hypogammaglobulinemia," New England Journal of Medicine, Massachusetts Medical Society, United States, May 23, 1968, vol. 278, pp. 1144-1146.
Herbst R., et al., "Folding of Firefly (*Photinus pyralis*) Luciferase: Aggregation and Reactivation of Unfolding Intermediates," Biochemistry, Apr. 17, 1998, vol. 37, No. 18, pp. 6586-6597.
Hershfield M., "Biochemistry and Immunology of Poly(ethylene glycol)-Modified Adenosine Deaminase (PEG-ADA)," In: ACS Symposium Series 680, Poly(ethylene glycol), Chemistry and Biological Applications, Harris J.M., and Zaplipsky S., eds., American Chemical Society, Washington, DC, Apr. 1997, pp. 145-154.
Hershfield M.S., et al., "Use of Site-Directed Mutagenesis to Enhance the Epitope-Shielding Effect of Covalent Modification of Proteins with Polyethylene Glycol," Proceedings of the National Academy of Sciences of the United States of America, Aug. 15, 1991, vol. 88, pp. 7185-7189.
Hess et al., "Cancer metabolism and oxidative stress: Insights into carcinogenesis and checmotherapy via the non-dihydrofolate reductase effects on methotrexate," BB Clinical 3, Jun. 2015, pp. 152-161.
Highlights of Prescribing Information for Allegra (fexofenadine hydrochloride) tablets, ODT 1-18, orally disintegrating tablets) and oral suspension, Jul. 31, 2007 (Apr. 31, 2007, pp. 1-19. Retrieved from the Internet www.accessdata.fda.gov/drugsatfda_docs/label/2008/020872s018,021963s0021bl.pdf on Nov. 7, 2020 (Nov. 7, 2020).
Hinds K., et al., "Synthesis and Characterization of Poly(Ethylene Glycol)-Insuline Conjugates," Bioconjugate Chemistry, American Chemical Society, United States, Feb. 15, 2000, vol. 11, pp. 195-201.
Hirel P., et al., "Extent of N-terminal Methionine Excision from *Escherichia coli* Proteins is Governed by the Side-Chain Length of the Penultimate Amino Acid," Proceedings of the National Academy of Sciences of the United States of America, Jul. 24, 1989, vol. 86, pp. 8247-8251.
"Horizon gets FDA approval for Krystexxa's use with methotrexate for uncontrolled gout," Seeking Alpha, Ravikash, SA News Editor, Jul. 8, 2022, 2 pages.
Horizon, "Horizon Therapeutics plc announces FDA has granted priority review of the supplemental biologics license application (sBLA) for the concomitant use of Krystexxa® (pegloticase injection) plus methotrexate for people living with uncontrolled gout," Mar. 7, 2022, 3 pages.
"Horizon's Krystexxa wins FDA combo nod to fight drug resistance," Fierce Pharm, Jul. 8, 2022, 3 pages.
"Horizon nabs FDA expanded label for gout med Krystexxa," Endpoints, Jul. 8, 2022, 2 pages.
"Horizon Therapeutics: FDA Approves Expanded Labeling for Krystexxa With Methotrexate," Nasdaq, Jul. 8, 2022, 1 page.
"Horizon Therapeutics: FDA approves expanded labeling for Krystexxa with methotrexate," RTTNews, Published Jul. 8, 2022, 5 pages.
"Horizon therapeutics receives FDA approval for uncontrolled gout candidate," Benzinga, Jul. 8, 2022, 7 pages.
Hortnagl H., et al., "Membrane Proteins of Chromaffin Granules, Dopamine-Hydroxylase, A Major Constituent," Biochemical Journal, Aug. 1972, vol. 129, No. 1, pp. 187-195.
Huse W.D., et al., "Generation of a Large Combinatorial Library of the Immunoglobulin Repertoire in Phage Lambda," Research Article, Dec. 8, 1989, vol. 246, pp. 1275-1281.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, Aug. 1988, vol. 85, pp. 5879-5883.
Inada Y., et al. "Biomedical and Biotechnological Applications of PEG- and PM-Modified Proteins," Trends Biotechnology, Elsevier Science Limited, Mar. 1995, vol. 13, pp. 86-91.
Information on EC 1.7.3.3—Urate Oxidase: Retrieved from URL: www.brenda-enzymes.org/php/flat.sub.—result.php4?ecno=1.7.3.3&organisms-ub.—list=&Suchword =, Date Jul. 20, 2009, 53 pages.
Ishino, K., et al., "Protein Concentration Dependence on Aggregation Behavior and Properties of Soybean 7S and 11S Globulins during Alkali-Treatment," Agricultural and Biological Chemistry, Jun. 1980, vol. 44, No. 6, pp. 1259-1266.
Ito M., et al., "Identification of an Amino Acid Residue Involved in the Substrate-binding Site of Rat Liver Uricase by Site-directed Mutagenesis," Biochemical and Biophysical Research Communications, Academic Press, United States, Aug. 31, 1992, vol. 187, pp. 101-107.
Jani et al., "The role of DMARDs in reducing the immunogenicity of TNF inhibitors in chronic inflammatory diseases," Rheumatology, 53(2), Feb. 2014, pp. 213-222.
Jaques L., "The Reaction of Heparin with Proteins and Complex Bases," Biochemical Journal, Jul. 1943, vol. 37, pp. 189-195.
Jones A., "The Isolation of Bacterial Nucleic Acids using Cetyltrimethylammonium Bromide," Biochimica et Biophysica Acta, Apr. 1953, vol. 10, pp. 607-612.
Kabat E.A., et al., "Sequences of Proteins of Immunological Interest," US Department of Health and Human Services, 1983, 4 Pages.
Kahn K., et al., "Kinetic Mechanism and Cofactor Content of Soybean Root Nodule Urate Oxidase," Biochemistry, American Chemical Society, United States, Apr. 15, 1997, vol. 36, pp. 4731-4738.
Karri et al., "Methotrexate and Leucovorin exposure modulates biochemical markers in female accessory reproductive organs of albino rats," General Endocrinology, Jul. 2012, pp. 369-386, doi: 10.4183/aeb.2012.369.
Kawata AK., et al., "Validation of the Sf-36 and Haq-Di in Patients With Treatment-Failure Gout," Annals of the Rheumatic Diseases, 2007, 66 (Suppl II), 236, Poster 359, 1 Page.
Keenan et al., "The effect of immunomodulators on the efficacy and tolerability of pegloticase: a systematic review," Seminars in Arthritis and Rheumatism, vol. 51, No. 2, Apr. 2021, pp. 347-352.
Keenan et al., "Use of Pre-Infusion Serum Uric Acid Levels as a Biomarker for Infusion Reaction Risk in Patients on Pegloticase," Rheumatology and Therapy, Jun. 2019, 6(2), pp. 299-304, Epub Mar. 14, 2019, https://pubmed.ncbi.nlm.nih.gov/30875075/.
Kelly S.J., et al., "Diabetes Insipidus in Uricase-Deficient Mice: A Model for Evaluating Therapy with Poly(Ethylene Glycol)-Modified Uricase," Journal of the American Society of Nephrology, Lippincott Williams & Wilkins, United States, May 2001, vol. 12, pp. 1001-1009.
Khanna et al., "2012 American College of Rheumatology Guidelines for Management of Gout Part I: Systematic Non-Pharmacologic and Pharmacologic Therapeutic Approaches to Hyperuricemia," Arthritis Care & Research, Oct. 2012, 64(10), pp. 1431-1466 (28 pages).
Khanna et al., "2012 American College of Rheumatology Guidelines for Management of Gout Part II: Therapy and Anti-Inflammatory Prophylaxis of Acute Gouty Arthritis," Arthritis Care & Research, Oct. 2012, 64(10), pp. 1447-1461 (23 pages).
Khanna et al., "Reducing Immunogenicity of Pegloticase (RECIPE) with Concomitant use of Mycophenolate Mofetil in Patients with Refractory Gout—a Phase II Double Blind Randomized Controlled Trial," ACR Convergence 2020, Abstract #0952, Nov. 2020, 5 pages.
Khanna et al., "Reducing Immunogenicity of Pegloticase (RECIPE) with Concomitant use of Mycophenolate Mofetil in Patients with Refractory Gout—a Phase II Double Blind Randomized Controlled

(56) References Cited

OTHER PUBLICATIONS

Trial," ACR Convergence Where Rheumatology Meets, Abstract #0952, Nov. 2020, Final Presentation, 17 pages.
Khanna et al., "Reducing Immunogenicity of Pegloticase with Concomitant use of Mycophenolate Mofetil in Patients with Refractory Gout: A Phase II, Randomized, Double-Blind, Placebo-Controlled Trial," Arthritis & Rheumatology, vol. 73, No. 8, Aug. 2021, pp. 1523-1532.
Kidney International, "Kidney Disease: Improving Global Outcomes (KDIGO) Guidelines," Aug. 2009, vol. 76, Supplement 113, 140 pages, https://kdigo.org/wp-content/uploads/2017/02/KDIGO-2009-CKD-MBD-Guideline-English.pdf.
Kinsella, J.E., et al., "Uricase From Fish Liver: Isolation and Some Properties," Comparative Biochemistry and Physiology, American Society of Zoologists, Division of Comparative Physiology, Elsevier, Great Britain, Dec. 30, 1985, vol. 82B, No. 4, pp. 621-624.
Kinstler O.B., et al., "Characterization and Stability of N-Terminally PEGylated rhG-CSF," Pharmaceutical Research, Plenum Publishing Corporation, United States, Jul. 1996, vol. 13, No. 7, pp. 996-1002.
Kishimoto et al., "Improving the efficacy and safety of biologic drugs with tolerogenic nanoparticles," Nature Nanotechnology 11, Aug. 2016, pp. 890-899.
Kissel P., et al., "Modification of Uricaemia and the Excretion of Uric Acid Nitrogen by an Enzyme of Fungal Origin," Nature, Jan. 6, 1968, vol. 217, pp. 72-74.
Kito M., et al., "A Simple and Efficient Method for Preparation of Monomethoxypolyethylene Glycol Activated with p-Nitrophenylchloroformate and its Application to Modification of L-Asparaginase," Journal of Clinical Biochemistry and Nutrition, Institute of Applied Biochemistry, Japan, Sep. 1996, vol. 21, pp. 101-111.
Kohler, G., et al., "Pillars Article: Continuous Cultures of Fused Cells Secreting Antibody of Predefined Specificity," Nature, Mar. 1975, vol. 256, No. 5517, pp. 495-497. The Journal of Immunology, Mar. 2005, 1:174(5):2453-2455.
Kontsek, P., et al., "Forty Years of Interferon," Acta Virologica, Slovak Academic Press, Slovak Republic, Dec. 1997, vol. 41, pp. 349-353.
Kozbor et al., "The production of monoclonal antibodies from human lymphocytes," Immunology Today, Mar. 1983, 4(3), pp. 72-79.
Kozma E.M., et al., "An Accumulation of Proteoglycans in Scarred Fascia," Molecular and Cellular Biochemistry, Jan. 2000, vol. 203, pp. 103-112.
Kozma et al., "Anti-PEG antibodies: Properties, formation, testing and role in adverse immune reactions to PEGylated nano-biopharmaceuticals," Advanced Drug Delivery Reviews, vols. 154-155, 2020, pp. 163-175.
Kral L.G., et al., "Cloning A cDNA For *Drosophila melanogaster* Urate Oxidase," Gene, Elsevier Science Publishers B.V, Netherlands, 1986, vol. 45, pp. 131-137.
Krieckaert, C.L. et al. "Methotrexate reduces immunogenicity in adalimumab treated rheumatoid arthritis patients in a dose dependent manner" Ann Rheum Dis, 71(11):1914-1915 (2012).
Krystexxa (pegloticase) [prescribing information] Horizon, Apr. 2012, 14 pages.
"Krystexxa plus methotrexate approved for uncontrolled gout," MedMDS, Jul. 8, 2022, 4 pages.
"Krystexxa plus methotrexate approved for uncontrolled gout," MPR, Jul. 8, 2022, 4 pages.
Kunitani M., et al., "Classical Light Scattering Quantitation Of Protein Aggregates: Off-line Spectroscopy Versus HPLC Detection," Journal of Pharmaceutical and Biomedical Analysis, Elsevier Science B.V., Netherlands, Dec. 1997, vol. 16, 16 Pages.
Kunitani M., et al., "On-Line Characterization of Polyethylene Glycol-Modified Proteins," Journal of Chromatography, Elsevier Science Ltd., Dec. 27, 1991, vol. 588, pp. 125-137.
Larsen K., "Purification of Nodule-Specific Uricase From Soybean by Arginine-Sepharose Affinity Chromatography," Preparative Biochemistry and Biotechnology, 1990, vol. 20, No. 1, 1 Page, (Abstract Only).
Laurent T.C., et al., "Fractionation of Hyaluronic Acid: The Polydispersity of Hyaluronic Acid from the Bovine Vitreous Body," Biochimica et Biophysica Acta, Aug. 26, 1960, vol. 42, pp. 476-485.
Lawrence R.C., et al., "Estimates of the Prevalence of Arthritis and Selected Musculoskeletal Disorders in the United States," Arthritis & Rheumatology, May 1998, vol. 41, No. 5, pp. 778-799.
Leach, M., et al., "Efficacy of Urate Oxidase (Uricozyme) in Tumor Lysis Induced Urate Nephropathy," Clinical & Laboratory Haematology, Blackwell Science Limited, Jun. 1998, vol. 20, pp. 169-172.
Leaustic M., et al., "Allergic Manifestation Of The Bronchospasm Type After Intravenous Injection Of Urate Oxidase In A Female Patient Treated For Myeloma," Rev Rhum Mal Osteoartic, 1983, vol. 50, No. 7, 5 Pages.
Lee et al., "Reduction in Serum Uric Acid May Be Related to Methotrexate Efficacy in Early Rheumatoid Arthritis: Data from the Canadian Early Arthritis Cohort (CATCH)," Clinical Medicine Insights: Arthritis and Musculoskeletal Disorders, Jan. 2016, vol. 9, pp. 37-43.
Lee C.C., et al., "Generation of cDNA Probes Directed by Amino Acid Sequence: Cloning of Urate Oxidase," Science, American Association for the Advancement of Science, United States, Mar. 4, 1988, vol. 239, No. 4844, pp. 1288-1291.
Lee et al., "THU0149 does methotrexate lower serum uric acid levels? Data from the catch cohort," Poster Presentations, Annals of the Rheumatic Diseases, Jun. 2015, vol. 74, pp. 248.
Lee, S-S., "Studies on Glycosaminoglycans in Tissues," Fukushima Journal of Medical Sciences, Jan. 1973, vol. 19, No. 1-4, pp. 33-39.
Lee T.H., et al., "A Novel Secretory Tumor Necrosis Factor-Inducible Protein (TSG-6) is a Member of the Family of Hyaluronate Binding Proteins, Closely Related to the Adhesion Receptor CD44," The Journal of Cell Biology, Jan. 1, 1992, vol. 116, No. 2, pp. 545-557.
Lee et al.; "Carboplatin hypersensitivity: a 6-h 12-step protocol effective in 35 desensitizations in patients with gynecological malignancies and mast cell/IgE-mediated reactions."; Gynecol Oncol 2004;95:370-6; Dated Mar. 5, 2004; 7 pages.
Legoux R., et al., "Cloning and Expression in *Eschericia coli* of the Gene Encoding Aspergillus Flavus Urate Oxidase," The Journal of Biological Chemistry, American Society for Biochemistry and Molecular Biology, United States, Apr. 25, 1992, vol. 267, No. 12, pp. 8565-8570.
Lie et al., "The effect of comedication with conventional synthetic disease modifying antirheumatic drugs on TNF inhibitor drug survival in patients with ankylosing spondylitis and undifferentiated spondyloarthritis: results from a nationwide prospective study," Annals of the Rheumatic Diseases, Jun. 2015;74(6), pp. 970-978.
Lim S.Y., et al., "Trends in Gout and Rheumatoid Arthritis Hospitalizations in the United States, 1993-2011," The Journal of the American Medical Association, Jun. 7, 2016, vol. 315, No. 21, pp. 2345-2347.
Lipsky P.E., et al., "Pegloticase Immunogenicity: The Relationship Between Efficacy and Antibody Development in Patients Treated for Refractory Chronic Gout," Arthritis Research & Therapy, Mar. 4, 2014, vol. 16, No. 2, R60, 8 Pages.
Lit, J-Y., et al., "Mutations at the S1 Sites of methionine Aminopeptidases From *Escherichia coli* and *Homo sapiens* Reveal the Residues Critical for Substrate Specificity," Journal of Biological Chemistry, May 14, 2004, vol. 279, No. 20, pp. 21128-21134.
Liu C., et al., "Prednisone in Uric Acid Lowering in Symptomatic Heart Failure Patients With Hyperuricemia (PUSH-PATH) Study," Canadian Journal of Cardiology, Sep. 2013, vol. 29, No. 9, pp. 1048-1054, Especially Abstract.
Li-Yu J., et al., "Treatment of Chronic Gout. Can We Determine When Urate Stores Are Depleted Enough to Prevent Attacks of Gout?," The Journal of Rheumatology, Mar. 2001, vol. 28, No. 3, pp. 577-580.
London M., et al., "Uricolytic Activity of Purified Uricase in Two Human Beings," Science, May 10, 1957, vol. 125, pp. 937-938.

(56) References Cited

OTHER PUBLICATIONS

Lundquist et al., "Psoriasis and Normouricemic Gout," Dermatology, 1982, vol. 164, No. 2, pp. 104-108.
Macart M., et al., "An Improvement of the Coomassie Blue Dye Binding Method Allowing An Equal Sensitivity To Various Proteins: Application To Cerebrospinal Fluid," Clinica Chimica Acta, Elsevier Biomedical Press, Jun. 16, 1982, vol. 122, pp. 93-101.
Maccari F., et al., "Glycosaminoglycan Blotting On Nitrocellulose Membranes Treated With Cetylpyridinium Chloride After Agarose-Gel Electrophoretic Separation," Electrophoresis, Sep. 2002, vol. 23, pp. 3270-3277.
Mahler H.R., et al., "Studies of Uricase. 1. Preparation, Purification, and Properties of a Cuproprotein," Journal of Biological Chemistry, American Society for Biochemistry and Molecular Biology, United States, Oct. 1955, vol. 216, pp. 625-641.
Mahmoud H.H., et al., "Advances in the Management of Malignancy-Associated Hyperuricaemia," British Journal of Cancer, Supplement 4, Churchill Livingstone, United Kingdom, Jun. 1998, vol. 77, pp. 18-20.
Majjhoo A., et al., "Prophylaxis for Infusion Reactions to Pegloticase: An Analysis of Two Different Corticosteroid Pre-Infusion Regimens in US Community Rheumatology Practices," ACR/ARHP Annual Meeting, Abstract No. 213, Prophylaxis to Pegloticase, Sep. 28, 2016, 4 Pages, Retrieved from URL: https://acrabstracts.org/abstract/.
Majjhoo et al., "Comparison of two corticosteriod pre-infusion regimes for pegloticase in the United States: A retrospective analysis in community rheumatology practices," Drugs Real World Outcomes, Dec. 2019;6(4):165-171.
Majjhoo et al., "Prophylaxis for Infusion Reactions to Pegloticase: An Analysis of Two Different Corticosteroid Pre-Infusion Regimens in US Community Rheumatology Practices," vol. 68, NJ, USA: Wiley, Poster, (2016), 1 page.
Malakhova E.A., et al., "Kinetic Properties of Bacterial Urate Oxidase Entrapped In Hydrated Reversed Micelles," Biologicheskie Membrany, 1991, vol. 8, No. 5, 1 Page, (Abstract Only).
Malamet et al., "SAT0355 Real World Risk of Infusion Reactions with Pegloticase Treatment: Findings from Post-Approval US Safety Data," Annals of the Rheumatic Diseases, Jun. 2013, 72(Suppl 3), pp. A703-A704, https://ard.bmj.com/content/72/Suppl_3/A703.3.
Male et al., "Immunology," 8th edition, Chapter 11, pp. 183-198 and Chapter 19, pp. 307-321, Philadelphia, PA, Elsevier Inc., 2013.
Martin et al., "Methotrexate in Psoriasis: Precipitation of Gout," Arch Dermatol., Oct. 1967, vol. 96, No. 4, pp. 431-433, doi:10.1001/archderm.1967.01610040081015.
Matsumura G., et al., "The Preparation of Hyaluronic Acid from Bovine Synovial Fluid," Short Communications, Biochimica et Biophysica Acta, Mar. 5, 1963, vol. 69, pp. 574-576.
Mcsweeney et al., "Pre-treatment with high molecular weight free PEG effectively suppresses anti-PEG antibody induction by PEG-liposomes in mice," Journal of Controlled Release, vol. 329, Jan. 10, 2021, pp. 774-781.
Milgroom, A et al., "Immunosuppressant Use and Gout in the Prevalent Solid Organ Transplant Population," Journal of the American Society of Nephrology, Oct. 2018, 29:152 Abstract TH-P0160, 3 pages.
Miura S., et al., "Urate Oxidase is Imported into Peroxisomes Recognizing the C-terminal SKL Motif of Proteins," European Journal of Biochemistry, Blackwell Science Ltd., United Kingdom, Jul. 1, 1994, vol. 223, pp. 141-146.
Moerschell R.P., et al., "The Specificities of Yeast Methionine Aminopeptidase and Acetylation of Amino-terminal Methionine in Vivo," Journal of Biological Chemistry, Nov. 15, 1990, vol. 265, No. 32, pp. 19638-19643.
Monkarsh, S.P., et al., "Positional Isomers Of Monopegylated Interferon Alpha-2a: Isolation, Characterization, And Biological Activity," Analytical Biochemistry, Academic Press, United States, May 1997, vol. 247, pp. 434-440.
Montagna, R., et al., "Letter to Editor," Nephrologie, 1990, vol. 11, No. 4, 259, 3 Pages.
Montalbini, P., et al., "Isolation And Characterization Of Uricase From Bean Leaves And Its Comparison With Uredospore Enzymes," Plant Science, Elsevier Science Ireland Ltd., Ireland, Sep. 1999, vol. 147, pp. 139-147.
Montalbini, P., et al., "Uricase From Leaves: Its Purification And Characterization From Three Different Higher Plants," Planta, Springer-Verlag, Germany, Jul. 1997, vol. 202, pp. 277-283.
Moolenburgh, J.D., et al., "Rasburicase Treatment In Severe Tophaceous Gout: A Novel Therapeutic Option," Clinical Rheumatology, Sep. 2006, vol. 25, pp. 749-752.
Moore, W.V., et al., "Role of Aggregated Human Growth Hormone (hGH) in Development of Antibodies to hGH," The Journal of Clinical Endocrinology and Metabolism, The Endocrine Society, United States, Oct. 1980, vol. 51, pp. 691-697.
Morrison, S. L., et al., "Chimeric human antibody molecules: mouse antigen-binding domains with human constant region domains", Proceedings of the National Academy of Sciences (1984); 81(21): 6851-6855.
Motojima, K., et al., "Cloning And Sequence Analysis of cDNA For Rat Liver Uricase," Journal of Biological Chemistry, Nov. 15, 1988, vol. 263, No. 32, pp. 16677-16681.
Mountain View Pharmaceuticals, Inc., "Puricase.Rtm.," U.S. Trademark Registration No. 2,246,623 (report obtained from U.S. Trademark Electronic Search System (TESS), Dec. 5, 2001), 1 page.
Mourad, G., et al., "Role of Anti-Urate Oxidase Precipitant Antibodies in Urate Oxidase Resistant Hyperuremic," La Presse Medicale, Nov. 24, 1984, vol. 13, No. 42, p. 2585.
Moussy, G., et al., "Inter-Species DNA Polymerase Delta Chimeras Are Functional In *Saccharomyces cerevisiae*," European Journal of Biochemistry, Jul. 1, 1995, vol. 231, No. 1, pp. 45-49.
Myers EW, et al. Optimal alignments in linear space. Bioinformatics. Mar. 1, 1988;4(1):11-17.
"N- and C-Terminally Truncated Pig-Baboon Chimeric Uricase (PBC-NT-CT)," Retrieved from EBI Accession No. GSP: AAY81255, Jun. 19, 2000, 2 Pages, XP002404208.
Nagata, S. et al., "Synthesis in *E. coli* of a polypeptide with human Leukocyte interferon activity," Nature, vol. 284, Mar. 1980, pp. 316-320.
Nahm B.H., et al., "Induction and De Novo Synthesis of Uricase, a Nitrogen-Regulated Enzyme in Neurospora Crassa," Journal for Bacteriology, American Society for Microbiology, United States, May 1987, vol. 169, No. 5, pp. 1943-1948.
Needleman, S.B. & Wunsch, C.D. "A general method applicable to the search for similarities in the amino acid sequences of two proteins." J. Mol. Biol. 48.3 (1970), pp. 443-453.
Neuberger M.S., et al., "Recombinant Antibodies Possessing Novel Effector Functions," Nature, Dec. 13, 1984, vol. 312, pp. 604-608.
Ngo, J.T., et al., "Computational Complexity, Protein Structure Prediction, And The Levinthal Paradox," The Protein Folding Problem and Tertiary Structure Prediction, Merz et al., (ed.), Birkhauser, Boston, MA, 1994, pp. 491-495.
Nishida Y., et al., "Hypouricaemic Effect After Oral Administration In Chickens Of Polyethylene Glycol-modified Uricase Entrapped In Liposomes," Journal of Pharmacy and Pharmacology, Pharmaceutical Press, United Kingdom, May 1984, vol. 36, pp. 354-355.
Nishimura, H., et al., "Improved Modification of Yeast Uricase with Polyethylene Glycol: Accompanied with Nonimmunoreactivity Towards Anti-Uricase Serum and High Enzymic Activity," Enzyme, Karger, Switzerland, 1981, vol. 26, pp. 49-53.
Nishimura H., et al., "Modification of Yeast Uricase with Polyethylene Glycol: Disappearance of Binding Ability towards Anti-Uricase Serum," Enzyme, Karger, Switzerland, 1979, vol. 24, pp. 261-264.
Nucci M.L., et al., "The Therapeutic Value of Poly(Ethylene Glycol)-Modified Proteins," Advanced Drug Delivery Reviews, Elsevier Science Publishers, Netherlands, Mar.-Apr. 1991, vol. 6, No. 2, pp. 133-151.
"$NZNP—Horizon gets FDA approval for Krystexxa's use with methotrexate for uncontrolled gout," Breaking News @MarketCurrents, Jul. 8, 2022, SANewsTwitter, 1 page.
Osman A.M., et al., "Liver Uricase In Camelus Dromedarius: Purification And Properties," Comparative Biochemistry and Physi-

(56) References Cited

OTHER PUBLICATIONS ology B, Pergamon Press, London, GB, Dec. 6, 1989, vol. 94B, No. 3, pp. 469-474, ISSN 0305-0491, XP002125210.
Otta M.E., et al., "Solubilization of Particle-Linked Urate Oxidase by Different Agents," Acta Physiologica Latinoamericana, 1975, vol. 25, pp. 451-457.
Pakula A.A., et al., "Genetic Analysis of Protein Stability and Function," Annual Review of Genetics, 1989, vol. 23, pp. 289-310.
Palleroni A.V., et al., "Interferon Immunogenicity: Preclinical Evaluation of Interferon-alpha.2a," Journal Of Interferon and Cytokine Research, Mary Ann Liebert, Inc., United States, Jul. 1997, vol. 17, Supplement 1, pp. S23-S27.
Pearce R.H., et al., "Quantitative Isolation of Purified Acidic Glycosaminoglycans from Rat Skin," Canadian Journal of Biochemistry and Physiology, Oct. 1967, vol. 45, pp. 1565-1576.
Perez-Ruiz F., et al., "Effect of Urate-Lowering Therapy on the Velocity of Size Reduction of Tophi in Chronic Gout," Arthritis & Rheumatology, Aug. 15, 2002, vol. 47, No. 4, pp. 356-360.
Philippovich, Y.B., "The Fundamentals of Biochemistry," AGAR, Moscow, Russia, 1999, pp. 29-30, (with unverified, Partial English language translation).
Pitts O.M., et al., "Uricase: Subunit Composition and Resistance to Denaturants," Biochemistry, American Chemical Society, United States, Feb. 26, 1974, vol. 13, No. 5, pp. 888-892.
Porstmann, B., et al., "Comparison of Chromogens for the Determination of Horseradish Peroxidase as a Marker in Enzyme Immunoassay," Journal of Clinical Chemistry and Clinical Biochemistry, Walter de Gruyter & Co., Germany, Jul. 1981, vol. 19, pp. 435-439.
Potaux L., et al., "Uricolytic Therapy Value of Urate Oxidase in the Treatment of Hyperuricemia," La Nouvelle Presse Medicale, Apr. 12, 1975, vol. 4, No. 15, 10 Pages.
"Prevent—Definition by Merriam-Webster Online Dictionary," pp. 1-3, [Retrieved on Jun. 27, 2013] Retrieved from URL: http://www.merriam-webster.com/dictionary/prevent.
Pui et al., "Recombinant Urate Oxidase for the Prophylaxis or Treatment of Hyperuricemia in Patients With Leukemia or Lymphoma," Journal of Clinical Oncology, vol. 19, Issue 3, Feb. 2001, pp. 697-704.
Pui et al., "Recombinant Urate Oxidase (rasburicase) in the prevention and treatment of malignancy-associated hyperuricemia in pediatric and adult patients: results of a compassionate-use trial," Leukemia Oct. 15, 2001, pp. 1505-1509.
Pui et al., "Urate oxidase in prevention and treatment of hyperusicemia associates with lymphoid malignancies," Leukemia Nov. 11, 1997, pp. 1813-1816.
R&D Focus Drug News: "PEG-uricase BioTechnology General, Duke University, Mountain View licensing agreement," DataStar File IPNR/IPNA, Accession No. 1998:2984 DRUGNL, Aug. 24, 1998, 1 Page.
Reinders, M., "Practice Research in the Field of Gout: Clinical Pharmacology of Antihyperuricemic Drugs", University of Groningen, Doctoral Thesis, Nov. 28, 2008, pp. 1-152. p. 18, Table 2; p. 131, para 2.
Richette P., et al., "Rasburicase for Tophaceous Gout not Treatable with Allopurinol: An Exploratory Study," The Journal of Rheumatology, Oct. 2007, vol. 34, No. 10, pp. 2093-2098.
Richette P., et al., "Successful Treatment with Rasburicase of a Tophaceous Gout in a Patient Allergic to Allopurinol," Nature Clinical Practice Rheumatology, Jun. 2006, vol. 2, No. 6, pp. 338-342.
Rinella J.V., et al., "Elutability of Proteins from Aluminum-Containing Vaccine Adjuvants by Treatment with Surfactants," Journal of Colloid and Interface Science, Jan. 1, 1998, vol. 197, pp. 48-56.
Rosenberg A.S., "Effects of Protein Aggregates: An Immunologic Perspective," The American Association of Pharmaceutical Scientists Journal, United States, Aug. 4, 2006, vol. 8, No. 3, pp. E501-E507.
Rosenberg A.S., et al., "Urate-Oxidase for the Treatment of Tophaceous Gout in Heart Transplant Recipients," Rev Rhum, Eng. Ed., May 1995, vol. 62, No. 5, pp. 392-394.
Rudinger, J., "Characteristics Of The Amino Acids As Components Of A Peptide Hormone Sequence," Peptide Hormones, JA Parsons Edition, University Park Press, Jun. 1976, pp. 1-7.
Saag et al. "Initial results of a clinical study to determine whether a tolerizing regimen of pegloticase can increase the frequency of subjects having sustained lowering of serum urate," American College of Rheumatology, Abstract 1141, Sep. 2017, 2 pages.
Saag K., et al., "FRI0240: Clinical Trial To Determine Whether Altering The Regimen Of Pegloticase Administration Can Increase The Frequency Of Subjects Having Sustained Lowering Of Serum Urate," Annals of Rheumatic Disease, Friday, Jun. 15, 2018, vol. 77, p. 661.
Saifer M.G.P., et al., "Improved Conjugation of Cytokines Using High Molecular Weight Poly(ethylene glycol): PEG-GM-CSF as a Prototype," Polymer Preprints, American Chemical Society, United States, Apr. 1997, vol. 38, pp. 576-577.
Saifer M.G.P., et al., "Plasma Clearance And Immunologic Properties of Long-Acting Superoxide Dismutase Prepared Using 35,000 to 120,000 Dalton Poly-Ethylene Glycol," Advances in Experimental Medicine and Biology, 1994, vol. 366, pp. 377-387.
Saito, S., "Coagulation and Peptization of Polyelectrolyte Solution by Detergent Ions. I," Kolloid-Zeitschrift, 1955, vol. 143, No. 2, 18 Pages.
Sakane T., et al., "Carboxyl-Directed Pegylation of Brain-Derived Neurotrophic Factor Markedly Reduces Systemic Clearance with Minimal Loss of Biologic Activity," Pharmaceutical Research, Plenum Publishing Corporation, United States, Aug. 1997, vol. 14, pp. 1085-1091.
Sartore L., et al., "Enzyme Modification by mPEG with an Amino Acid or Peptide as Spacer Arms," Applied Biochemistry and Biotechnology, Jan. 1991, vol. 27, No. 1, pp. 45-54.
Savoca K., et al., "Induction of Tolerance in Mice by Uricase and Monomethoxypolyethylene Glycol-Modified Uricase," International Archives Of Allergy And Applied Immunology, 1984, vol. 75, pp. 58-67.
Scandella, C.J., et al., "A Membrane-Bound Phospholipase Al Purified from *Escherichia colt*," Biochemistry, Nov. 23, 1971, vol. 10, No. 24, pp. 4447-4456.
Schiavon O., et al., "Therapeutic Proteins: A Comparison Of Chemical And Biological Properties Of Uricase Conjugated To Linear Or Branched Poly(Ethylene Glycol) And Poly(N-Acryloylmorpholine)," Il Farmaco, Apr. 2000, vol. 55, No. 4, pp. 264-269.
Schinzel R., et al., "The Phosphate Recognition Site Of *Escherichia coli* Maltodextrin Phosphorylase," Federation of European Biochemical Societies, Jul. 1991, vol. 286, No. 1, 2, pp. 125-128.
Schlensinger et al., "Enhancing the response rate to recombinant uricases in patients with gout," BioDrugs, Mar. 2022, 36(2), pp. 95-103.
Schlensinger et al., "Pegloticase," Nature Reviews: Drug Discovery, vol. 10, Jan. 2011, pp. 17-18.
Schlesinger et al., "Evaluation of proposed criteria for remission and evidence-based development of criteria for complete response in patients with chronic refractory gout," ACR Open Rheumatology, Jun. 2019, vol. 1, No. 4, pp. 236-243, doi: 10.1002/acr2.1025.
Schumacher H.R., et al., "Effects of Febuxostat Versus Allopurinol and Placebo in Reducing Serum Urate in Subjects with Hyperuricemia and Gout: A 28-Week, Phase III, Randomized, Double-Blind, Parallel-Group Trial," Arthritis & Rheumatism (Arthritis Care & Research), Nov. 15, 2008, vol. 59, No. 11, pp. 1540-1548.
Schumacher, H.R., et al., "Outcome Evaluations in Gout," The Journal of Rheumatology, Jun. 2007, vol. 34, No. 6, pp. 1381-1385, XP008158539.
Scott, J., "The Precipitation of Polyanions by Long-Chain Aliphatic Ammonium Salts," Journal of Biochemistry, 1961, vol. 81, pp. 418-424.
Scott, J., "The Reaction of Long-Chain Quarternary Ammonium Salts with Acidic Polysaccharides," Chemistry and Industry, Feb. 12, 1955, pp. 168-169.

(56) References Cited

OTHER PUBLICATIONS

Scott, J., "The Solubility of Cetylpyridinium Complexes of Biological Polyanions in Solution of Salts," Biochimica et Biophysica Acta, Nov. 1955, vol. 18, pp. 428-429.
Scott, J.E., "Aliphatic Ammonium Salts in the Assay of Acidic Polysaccharides from Tissues," Methods Of Biochemical Analysis, Jan. 1960, vol. 8, pp. 145-197.
Serafini-Fracassini A., et al., "The Protein-Polysaccharide Complex of Bovine Nasal Cartilage," Journal of Biochemistry, Nov. 1967, vol. 105, pp. 569-575.
Sharma B., "Immunogenicity of Therapeutic Proteins. Part 3: Impact of Manufacturing Changes," Biotechnology Advances, Elsevier Inc., Netherlands, Jan. 2007, vol. 25, pp. 325-331.
Shearwater Polymers Inc:, "Functionalized Biocompatible Polymers for Research and Pharmaceuticals," Shearwater Polymers, Inc., Catalog, Jul. 1997, 6 Pages.
Sherman, F., et al., "Methionine or Not Methionine at the Beginning of a Protein," Bio Essays, Jul. 1985, vol. 3, Issue 1, pp. 27-31.
Sherman, M., et al., "Conjugation of High-Molecular Weight Poly(ethylene glycol) to Cytokines: Granulocyte-Macrophage Colony-Stimulating Factors as Model Substrates," ACS Symposium Series 680, Poly(ethylene glycol), Chemistry and Biological Applications, Harris J.M., and Zaplipsky S., eds., American Chemical Society, Washington, DC, Aug. 5, 1997, pp. 155-169.
Sherman, M., et al., "PEG-Uricase in the Management of Treatment-Resistant Gout and Hyperuricemia," Advanced Drug Delivery Reviews, Jan. 3, 2008, vol. 60, No. 1, pp. 59-68.
Shoji A., et al., "A Retrospective Study of the Relationship Between Serum Urate Level and Recurrent Attacks of Gouty Arthritis: Evidence for Reduction of Recurrent Gouty Arthritis With Antihyperuricemic Therapy," Arthritis & Rheumatology, Jun. 15, 2004, vol. 51, No. 3, pp. 321-325.
Sigma Catalog, p. 1008, Product Nos. U 3250, 292-8, U3500, U 9375 or U 3377, (1993), 2 pages.
Sigma Genosys: "Designing Custom Peptides," Accessed on Dec. 16, 2004, pp. 1-2.
Smith T., et al., "Human Lung Tryptase," Journal of Biological Chemistry, Sep. 10, 1984, vol. 259, No. 17, pp. 11046-11051.
Smolenska et al., "Effect of methotrexate on blood purine and pyrimidine levels in patients with rheumatoid arthritis," Rheumatology, Oct. 1999, vol. 38, No. 10, pp. 997-1002.
Somack R., et al., "Preparation of Long-Acting Superoxide Dismutase Using High Molecular Weight Polyethylene Glycol (41,000-72,000 Daltons)," Free Radical Research Communications, Harwood Academic Publishers GmBH, Germany, 1991, vol. 12-13, pp. 553-562.
Sorensen L.B., "Suppression of the Shunt Pathway in Primary Gout by Azathioprine," Proceedings of the National Academy of Science of the USA, Mar. 1966, vol. 55, No. 3, pp. 571-575.
Sparks et al., "Effect of Low-Dose Methotrexate on eGFR and Kidney Adverse Events: A Randomized Clinical Trial," Journal of the American Society of Nephrology, Dec. 2021, 32(12):3197-3207.
Stamp et al., "Expert opinion on emerging urate-lowering therapies," Expert Opinion on Emerging Drugs, vol. 23, 2018, pp. 201-209.
Strand et al., "Immunogenicity of Biologics in Chronic Inflammatory Diseases: A Systematic Review," BioDrugs, Aug. 2017, 31(4):299-316.
Streuli, M. et al., "Target cell specificity of two species of human interferon-α produced in *Escherichia coli* and of hybrid molecules derived from them," Proceedings of the National Academy of Sciences USA, vol. 78, No. 5, May 1981, pp. 2848-2852.
Sundy J., et al., "A Multicenter Longitudinal Study of Disease Characteristics in Patients With Treatment-Failure Gout," Presented at the EULAR—Annual European Congress of Rheumatology, Amsterdam, Netherlands, Poster 518, Jun. 21-24, 2006, 1 Page.
Sundy J., et al., "A Phase 2 Study of Multiple Doses of Intravenous Polyethylene Glycol (PEG)-uricase in Patients with Hyperuricemia and Refractory Gout," Presented at the EULAR—Annual European Congress of Rheumatology, Amsterdam, Netherlands, Poster 516, Jun. 21-24, 2006, 1 Page.
Sundy, J., et al., "A Phase I Study of Pegylated-Uricase (Puricase. RTM.) in Subjects with Gout," Presented at American College of Rheumatology Annual Scientific Meeting at San Antonio, TX, on Oct. 16-21, 2004, Poster 807, 1 page.
Sundy J., et al., "Efficacy and Tolerability of Pegloticase for the Treatment of Chronic Gout in Patients Refractory to Conventional Treatment: Two Randomized Controlled Trials," American Medical Association, Aug. 17, 2011, vol. 306, No. 7, pp. 711-720.
Sundy J., et al., "Pharmacokinetics and Pharmacodynamics of Intravenous PEGylated Recombinant Mammalian Urate Oxidase in Patients With Refractory Gout," Arthritis & Rheumatology, Mar. 2007, vol. 56, No. 3, pp. 1021-1028.
Sundy J., et al., "Quality of Life in Patients With Treatment-Failure Gout," Presented at the EULAR—Annual European Congress of Rheumatology, Amsterdam, Netherlands, Poster 517, Jun. 21-24, 2006, 1 Page.
Sundy J., et al., "Reduction of Plasma Urate Levels Following Treatment with Multiple Doses of Pegloticase in Patients with Treatment-Failure Gout," Arthritis & Rheumatism, Sep. 2008, vol. 58, No. 9, pp. 2882-2891.
Sundy J., et al., "Uricase and Other Novel Agents for the Management of Patients With Treatment-Failure Gout," Current Rheumatology Reports, Jun. 2007, vol. 9, No. 3, pp. 258-264.
Sundy, J.S., et al., "A Phase 2 Study of Multiple Doses of Intravenous Polyethylene Glycol (PEG)-uricase in Patients with Hyperuricemia and Refractory Gout," Presented at American College of Rheumatology 2005 Annual Scientific Meeting at San Diego, CA, #1836 on Nov. 13-17, 2005, 51 pages.
Sundy S., et al., Arthritis & Rheumatism, Sep. 2005, vol. 52, No. 9 (Supplement), Abstract Supplement, Annual Scientific Meeting, San Diego, California, Nov. 12-17, 2005, Abstract #1836, 3 Pages.
Sutterlin, et al., "Mixtures of Quaternary Ammonium Compounds and Anionic Organic Compounds in the Aquatic Environment: Elimination and Biodegradability in the Closed Bottle Test Monitored by LC-MS/MS," Chemosphere, Jun. 2008, vol. 72, No. 3, pp. 479-484, Abstract only.
Suzuki, H., et al., "Soybean Nodule-Specific Uricase (Nodulin-35) is Expressed and Assembled into a Functional Tetrameric Holoenzyme in *Escherichia coli*," Plant Physiology, American Society of Plant Physiologists, United States, Feb. 1991, vol. 95, pp. 384-389.
Takeda, et al., "Construction of Chimaeric Processed Immunoglobulin Genes Containing Mouse Variable and Human Constant Region Sequences," Nature, Apr. 4, 1985, vol. 314, pp. 452-454.
Talkington et al., "High MW polyethylene glycol prolongs circulation of pegloticase in mice with anti-PEG antibodies," Journal of Controlled Release, vol. 338, Oct. 10, 2021, pp. 804-812.
Terkeltaub R., "Gout", Clinical Practice, The New England Journal of Medicine, 2003, vol. 349, No. 17, pp. 1647-1655.
"The @US_FDA's decision on the co-treatment of pegloticase (#Krystexxa) plus methotrexate (#MTX) for patients with uncontrolled #gout was based on the phase 4 MIRROR clinical trial," HCPLive Tweet Twitter, Jul. 8, 2022, 1 page.
"The @US_FDA expanded the #pegloticase label to include the co-treatment of pegloticase (Krystexxa) injection plus methotrexate in patients with uncontrolled #gout. @HorizonNews," Rheumatology Network Tweet Tweeter, Jul. 8, 2022, 1 page.
Thomas et al., "Comparative Immunogenicity of TNF Inhibitors: Impact on Clinical Efficacy and Tolerability in the Management of Autoimmune Diseases. A Systematic review and Meta-Analysis," BioDrugs 29, Aug. 2015, pp. 241-258.
Tla S., et al., "Urate Oxidase from Pig Liver: Biochemical and Immunological Properties," Prikl Biokhim Mikrobiol, Izdatesltvo Nauka, Russia, Jul. 1, 1978, vol. 14, pp. 533-542.
Tomanee P., et al., "Fractionation of Protein, RNA, and Plasmid DNA in Centrifugal Precipitation Chromatography Using Cationic Surfactant CTAB Containing Inorganic Salts NaCl and NH4Cl," Wiley InterScience, Sep. 9, 2004, 8 Pages, DOI: 10.1002/bit.20203.
Top 10 Home Remedies: "How to Control Uric Acid Levels," Accessed on Sep. 22, 2015, pp. 1-6, Retrieved from URL: http://www.top10homeremedies.com/how-to/control-uric-acid-levels.html.

(56) References Cited

OTHER PUBLICATIONS

Treuheit M., et al., "Inverse Relationship of Protein Concentration and Aggregation," Pharmaceutical Research, Plenum Publishing Corporation, United States, Apr. 2002, vol. 19, pp. 511-516.
Truscoe R., "Effect of Detergents on Extraction and Activity of Ox-Kidney Urate Oxidase," Enzymologia, Jul. 31, 1967, vol. 33, pp. 119-132.
Truscoe R., et al., "Effect of pH on Extraction and Activity of Ox-kidney Urate Oxidase," Biochimica et Biophysica Acta, Elsevier Publishing Co., Netherlands, Jul. 8, 1964, vol. 89, pp. 179-182.
Tsuji J., et al., "Studies on Antigenicity of the Polyethylene Glycol (PEG)-Modified Uricase," International Journal of Immunopharmacology, Elsevier Science, 1985, vol. 7, No. 5, pp. 725-730.
Tsunasawa S., et al., "Amino-terminal Processing of Mutant Forms of Yeast Iso-1-cytochrome c, The Specificities of Methionine Aminopeptidase and Acetyltransferase," The Journal of Biological Chemistry, May 10, 1985, vol. 260, No. 9, pp. 5382-5391.
Tutton, R. et. al., "Pharmacogenomic Biomarkers in Drug Labels: What do they tell us?," Pharmacogenomics, Feb. 2014, 15(3), pp. 297-304.
U.S. Trademark Registration No. 2,246,623, entitled "Puricase," filed on Jul. 15, 1997, 1 Page.
Van Groen et al., "Application of the health assessment questionnaire disability index to various rheumatic diseases," Quality of Life Research, Nov. 2010, 19, pp. 1255-1263.
Varelas J., et al., "Expression and Characterization of a Single Recombinant Proteoglycan Tandem Repeat Domain of Link Protein That Binds Zinc and Hyaluronate," Archives of Biochemistry and Biophysics, Aug. 1, 1995, vol. 321, No. 1, pp. 21-30.
Venkataseshan V., et al., "Acute Hyperuricemic Nephropathy and Rental Failure after Transplantation," Nephron, Karger AG, Switzerland, 1990, vol. 56, pp. 317-321.
Verhoef et al., "Potential induction of anti-PEG antibodies and complement activation toward PEGylated therapeutics," Drug Discovery Today, vol. 19, Issue 12, Dec. 2014, pp. 1945-1952.
Verma et al., "Folate Conjugated Double Liposomes Bearing Prednisolone and Methotrexate for Targeting Rheumatoid Arthritis," Pharmaceutical Research, Aug. 2019, 36(8):123, pp. 1-13.
Vermeire et al., "Effectiveness of concomitant immunosuppresive therapy in suppressing the formation of antibodies to infliximab in Crohn's disease," Gut, Jan. 2007, vol. 56, pp. 1226-1231.
Veronese F., "Branched and Linear Poly(Ethylene) Glycol: Influence of the Polymer Structure on Ezymological, Pharmacokinetic, and Immunological Properties of Protein Conjugates," Journal of Bioactive and Compatible Polymers, Tectonic Publishing Co., Inc., United States, Jul. 1, 1997, vol. 12, pp. 196-207.
Veronese F., et al., "New Synthetic Polymers for Enzyme and Liposome Modification," In: ACS Symposium Series 580, Poly(Ethylene Glycol) Chemistry and Biological Applications, Harris J.M., and Zaplipsky S., eds., American Chemical Society, Washington, D.C., 1997, pp. 182-192.
Veronese F., et al., "Surface Modification of Proteins. Activation of Monomethoxy-Polyethylene Glycols by Phenylchloroformates and Modification of Ribonuclease and Superoxide Dismutase," Applied Biochemistry and Biotechnology, The Humana Press, Inc., United States, Apr. 1985, vol. 11, pp. 141-152.
Veronese F.M., et al., "Preface: Introduction and Overview of Peptide and Protein Pegylation," Advanced Drug Delivery Reviews, 2002, vol. 54, pp. 453-456.
Voet D., et al., Biochemistry, Second Edition, John Wiley & Sons, Inc., Apr. 1995, pp. 235-241.
Voshaar M. et al., "Dutch Translation and Cross-Cultural Adaptation of the PROMIS Physical Function Item Bank and Cognitive Pre-Test in Dutch Arthritis Patients," Arthritis Research & Therapy, Mar. 5, 2012, vol. 14, No. 2, 7 Pages.
Wallrath L., et al., "Molecular Characterization of the *Drosophila melanogaster* Rate Oxidase Gene, an Ecdysone-Repressible Gene Expressed Only in the Malpighian Tubules," Molecular and Cellular Biology, American Society for Microbiology, United States, Oct. 1990, vol. 10, pp. 5114-5127.
Waltrip R., et al., "Pharmacokinetics and Pharmacodynamics of Peg-Uricase in Patients With Hyperuricemia and Treatment Failure Gout," Presented at the EULAR—Annual European Congress of Rheumatology, Barcelona, Spain, Poster 358, Jun. 13-16, 2007, 2 Pages.
Waltrip R., et al., "Weekly Flare Burden Index: A New Metric for Evaluating Gout Treatment," Annals of the Rheumatic Diseases, 2007, vol. 66 (Suppl II), Abstract 748, p. 624.
Wang L., et al., "Purification and Characterization of Uricase, a Nitrogen-Regulated Enzyme, from Neurospora Crassa," Archives of Biochemistry and Biophysics, Academic Press, Inc., United States, Apr. 15, 1980, vol. 201, pp. 185-193.
Wang X., et al., "Rat Urate Oxidase: Cloning and Structural Analysis of the Gene and 5'-Flanking Region," Gene, Elsevier Science Publishers B.V., The Netherlands, Jan. 15, 1991, vol. 97, pp. 223-229.
Wang X.D., et al., NCBI Entrez Protein (PRF) Database, Deposited Sequence For Rat Urate Oxidase (NP 446220), National Library of Medicine, National institutes of Health, Accession No. 20127395, Accessed at http://www.ncbi.nlm.nih.gov/protein/20127395 , Accessed on Dec. 10, 2003, 2 pages.
Ward E.S., et al., "Binding Activities of a Repertoire of Single Immunoglobulin Variable Domains Secreted from *Escherichia coli*," Nature, Oct. 12, 1989, vol. 341, No. 6242, pp. 544-546.
Watanabe T., et al., "A Simple Purification Method for Rat Liver Urate Oxidase," Analytical Biochemistry, Academic Press, Inc., United States, Sep. 1978, vol. 89, No. 2, pp. 343-347.
WHO Drug Information, vol. 21, No. 4, 2007, List 98, p. 344.
Wortmann R., et al., "Gout and Hyperuricemia," Kelley's Textbook of Rheumatology, Edited by Ruddy S., Harris E., Sledge C., 6th edn. St. Louis: W.B. Saunders, 2001, pp. 1339-1371.
Wu, E.Q., et al., "Comorbidity Burden, Healthcare Resource Utilization, and Costs in Chronic Gout Patients Refractory to Conventional Urate-Lowering Therapy," American Journal of Therapeutics, Nov. 2012, vol. 19, No. 6, pp. e157-e166.
Wu X., et al., "Hyperuricemia and Urate Nephropathy in Urate Oxidase-Deficient Mice," Proceedings of the National Academy of Sciences, USA, National Academy of Sciences, United States, Jan. 18, 1994, vol. 91, No. 2, pp. 742-746.
Wu X., et al., "Two Independent Mutational Events in the Loss of Urate Oxidase during Hominoid Evolution," Journal of Molecular Evolution, Springer-Verlag, Germany, Jan. 1992, vol. 34, No. 1, pp. 78-84.
Wu X., et al., "Urate Oxidase: Primary Structure and Evolutionary Implications," Proceedings of the National Academy of Sciences, USA, Dec. 1989, vol. 86, No. 23, pp. 9412-9416.
Wuthrich, H. et al., "Guidelines for the Treatment of Gout: A Swiss Perspective," Swiss Medical Weekly 146, (Year: 2016), pp. 1-7.
Yamamoto K., et al., "Nucleotide Sequence of the Uricase Gene from *Bacillus* sp. TB-90," Journal of Biochemistry, Oxford University Press, England, Jan. 1996, vol. 119, No. 1, pp. 80-84.
Yamanaka H., et al., "Optimal Range of Serum Urate Concentrations to Minimize Risk of Gouty Attacks during Anti-Hyperuricemic Treatment," Advances in Experimental Medicine and Biology, 1998, vol. 431, pp. 13-18.
Yasuda Y., et al., "Biochemical and Biopharmaceutical Properties of Macromolecular Conjugates of Uricase with Dextran Polyethylene Glycol," Chemical and Pharmaceutical Bulletin, Pharmaceutical Society of Japan, Jul. 1990, vol. 38, No. 7, pp. 2053-2056.
Yeldandi A.V., et al., "Human Urate Oxidase Gene: Cloning and Partial Sequence Analysis Reveal a Stop Codon within the Fifth Exon," Biochemica et Biophysica Research Communication, Academic Press, United States, Sep. 14, 1990, vol. 171, No. 2, pp. 641-646.
Yelverton, E., et al., "Bacterial Synthesis of a Novel Human Leukocyte Interferon," Nucleic Acids Research, Feb. 11, 1981, vol. 9, No. 3, pp. 731-741.
Yokoyama S., et al., "Rapid Extraction of Uricase from Candida Utilis Cells by Use of Reducing Agent Plus Surfactant," Enzyme and Microbial Technology, Jan. 1988, vol. 10, No. 1, pp. 52-55.
Yue, C.S., et al., Population Pharmacokinetic and Pharmacodynamic Analysis of PEG-uricase in Subjects With Hyperuricemia and

(56) References Cited

OTHER PUBLICATIONS

Refractory Gout, presented at the American College of Clinical Pharmacy 2006 Annual Meeting on Oct. 26-29, 2006 at St. Louis, Missouri, Poster, 1 page.
Zhang, T., et al., "Affinity Extraction of BSA with Reversed Micellar System Composed of Unbound Cibacron Blue," Biotechnology Progress, Nov.-Dec. 1999, vol. 15, No. 6, pp. 1078-1082.
Zhang, W., et al., "Forward and Backward Extraction of BSA using Mixed Reverse Micellar System of CTAB and Alkyl Halides," Biochemical Engineering Journal, Oct. 2002, vol. 12, No. 1, pp. 1-5.
Zhu J., et al., "Can Dynamic Contrast-Enhanced MRI (DCE-MRI) and Diffusion-Weighted MRI (DW-MRI) Evaluate Inflammation Disease," A Preliminary Study of Crohn's Disease, Medicine (Baltimore), Apr. 2016, vol. 95, No. 14, Article e3239, pp. 1-9.
Freyne, B., "A Case Report of Immunosuppressant Medication-Associated Polyarticular Tophaceous Gout Successfully Treated Using the Polyethylene Glycol-Conjugated Uricase Enzyme Pegloticase", Transplant Proc., 50(10):4099-101, (2018).
Harrold LR, Andrade SE, Briesacher BA, Raebel MA, Fouayzi H, Yood RA, Ockene IS. Adherence with urate-lowering therapies for the treatment of gout. Arthritis Res Ther. 2009;11(2):R46.
Hong D. Desensitization for Allergic Reactions to Chemotherapy. Yonsei Med J Feb. 2019;60(2):119-125.
Huddleston, Edward M., and Angelo L. Gaffo. "Emerging strategies for treating gout." Current Opinion in Pharmacology 65 (2022): 102241.
Savient Pharmaceuticals, Inc.; Horizon. (2012). "Krystexxa: Highlights of prescribing information". Lake Forest, IL: Author; dated Apr. 2012; 14 pages.
Sulaiman, Narisa, et al. "Successful febuxostat desensitization in a patient with febuxostat hypersensitivity: a Malaysian experience." SAGE open medical case reports 5 (2017): 2050313X17749080.
Office Action issued in U.S. Appl. No. 18/409,450, dated Mar. 29, 2024.
International Search Report and Written Opinion issued for Application No. PCT/US2023/079369, dated Mar. 5, 2024.
So, Alexander, et al. "Canakinumab for the treatment of acute flares in difficult-to-treat gouty arthritis: results of a multicenter, phase II, dose-ranging study." Arthritis & Rheumatism 62.10 (2010): 3064-3076.
Schlesinger, Naomi, et al. "Canakinumab for acute gouty arthritis in patients with limited treatment options: results from two randomised, multicentre, active-controlled, double-blind trials and their initial extensions" Annals of the rheumatic diseases 71.11 (2012): 1839-1848.
Schumacher Jr, H. Ralph, et al. "Rilonacept (interleukin-1 trap) in the prevention of acute gout flares during initiation of urate-lowering therapy: results of a phase II randomized, double-blind, placebo-controlled trial." Arthritis & Rheumatism 64.3 (2012): 876-884.
Pillinger, Michael H., and Brian F. Mandell. "Therapeutic approaches in the treatment of gout." Seminars in Arthritis and Rheumatism. vol. 50. No. 3. WB Saunders, 2020.
Administration Food and Drug. AAC Briefing Document Krystexxa (Pegloticase). 2009. Mar. 23, 2016.
Albert JA, Hosey T, LaMoreaux B. Increased efficacy and tolerability of pegloticase in patients with uncontrolled gout co-treated with methotrexate: a retrospective study. Rheumatol Ther. 2020;7:639-48.
Baraf H. S., Matsumoto A. K., Maroli A. N., Waltrip R. W., 2nd. Resolution of gouty tophi after twelve weeks of pegloticase treatment. Arthritis Rheum. 2008;58(11):3632-4.
Baraf HS, Yood RA, Ottery FD, Sundy JS, Becker MA. Infusion-related reactions with pegloticase, a recombinant uricase for the treatment of chronic gout refractory to conventional therapy. J Clin Rheumatol. 2014;20:427-32.
Becker MA, Schumacher HR, Benjamin KL, Gorevic P, Greenwald M, Fessel J, et al. Quality of life and disability in patients with treatment-failure gout. J Rheumatol. 2009;36:1041-8.
Botson JK, Peterson J. Pretreatment and coadministration with methotrexate improved durability of pegloticase response: an observational, proof-of-concept case series. J Clin Rheum. 2022;28(1):e129-34.
Botson JK, Tesser JRP, Bennett R, Kenney HM, Obermeyer KO, LaMoreaux B, et al. Pegloticase in combination with methotrexate in patients with uncontrolled gout: a multicenter, open-label study (MIRROR). J Rheumatol. 2021;48:767-74.
Botson, John K., et al. "A randomized, placebo-controlled study of methotrexate to increase response rates in patients with uncontrolled gout receiving pegloticase: primary efficacy and safety findings." Arthritis & Rheumatology 75.2 (2023): 293-304.
Brook RA, Forsythe A, Smeeding JE, Lawrence Edwards N. Chronic gout. epidemiology, disease progression, treatment and disease burden. Curr Med Res Opin. 2010;26:2813-21.
Chen JH, Lan JL, Cheng CF, Liang WM, Lin HY, Tsay GJ, et al. Effect of urate-lowering therapy on all-cause and cardiovascular mortality in hyperuricemic patients without gout. A case-matched cohort study PloS One. 2015;10:e0145193.
Choi HK, Curhan G. Independent impact of gout on mortality and risk for coronary heart disease. Circulation. 2007;116:894-900.
Choi HK, Ford ES, Li C, Curhan G. Prevalence of the metabolic syndrome in patients with gout: the third national health and nurtrition examination survey. Arthritis Care Res (Hoboken). 2007;57:109-15.
Cimzia (certolizumab pegol) [package insert]. Smyrna: UCB, Inc.; 2016.
Copur S, Demiray A, Kanbay M. Uric acid in metabolic syndrome: does uric acid have a definitive role? Eur J Intern Med. 2022;S0953-6205(22):00165-0 (Epub ahead of print).
Culleton BF, Larson MG, Kannel WB, Levy D. Serum uric acid and risk for cardiovascular disease and death: the Framingham Heart Study. Ann Intern Med. 1999;131:7-13.
Dalbeth N, Nicolaou S, Baumgartner S, Hu J, Fung M, Choi HK. Presence of monosodium urate crystal deposition by dual-energy CT in patients with gout treated with allopurinol. Ann Rheum Dis. 2018;77:364-70.
Dervieux T, Orentas Lein D, Marcelletti J, Pischel K, Smith K, Walsh M, Richerson R. HPLC determination of erthrocyte methotrexate polyglutamates after low-dose methotrexate therapy in patients with rheumatoid arthritis. Clin Chem. 2003;49:1632-41.
Fels E, Sundy JS. Refractory gout: what is it and what to do about it? Current Opin Rheumatol. 2008;20:198-202.
FitzGerald JD, Dalbeth N, Mikuls T, Brignardello-Petersen R, Guyatt G, Abeles AM, et al. 2020 american college of rheumatology guideline for the management of gout. Arthritis Care Res (Hoboken). 2020;72:744-60.
Food and Drug Administration Arthritis Advisory Committee. Krystexxa™ (pegloticase) for intravenous infusion BLA No. 125293 2009.
Gaffo AL, Schumacher HR, Saag KG, Taylor WJ, Dinnella J, Outman R, et al. Developing a provisional definition of flare in patients with established gout. Arthritis Rheum. 2012;64:1508-17.
Gaffo, AL et al. (2018) Validation of A Definition For Flare In Patients With Established Gout Arthritis Rheumatol 70(3):462-467.
Hershfield MS, Ganson NJ, Kelly SJ, Scarlett EL, Jaggers DA, Sundy JS. Induced and pre-existing anti-polyethylene glycol antibody in a trial of every 3-week dosing of pegloticase for refractory gout, including in organ transplant recipients. Arthritis Res Ther. 2014;16:R63.
Horizon Therapeutics. News release Jul. 8, 2022.
Humira (adalimumab) [package insert]. North Chicago: AbbVie Inc.; 2021.
Keenan RT, Baraf HSB, LaMoreaux B. Use of pre-infusion serum uric acid levels as a biomarker for infusion reaction risk in patients on pegloticase. Rheumatol Ther. 2019;6:299-304.
Khanna P, Khanna D, Cutter G, Foster J, Melnick J, Jaafar S, et al. Reducing immunogenicity of pegloticase with concomitant use of mycophenolate mofetil in patients with refractory gout: a phase II, randomized, double-blind, placebo-controlled trial. Arthritis Rheumatol. 2021;73(8):1523-32 (Epub ahead of print).

(56) References Cited

OTHER PUBLICATIONS

Khanna P., Khanna D., Storgard C., Baumgartner S., Morlock R. A world of hurt: failure to achieve treatment goals in patients with gout requires a paradigm shift. Postgrad Med. 2016;128(1):34-40.
Kim SY, Guevara JP, Kim KM, Choi HK, Heitjan DF, Albert DA. Hyperuricemia and risk of stroke: a systematic review and meta-analysis. Arthritis Rheum. 2009;61:885-92.
Kingsbury SR, Conaghan PG, McDermott MF. The role of the NLRP3 inflammasome in gout. J Inflamm Res. 2011;4:39-49.
LaMoreaux B, Francis-Sedlak M, Svensson K, Holt R. Immunomodulation co-therapy with pegloticase: database trends 2014-2019 [abstract]. Ann Rheum Dis. 2020;79(suppl 1):108.
Lipsky PE, Calabrese LH, Kavanaugh A, Sundy JS, Wright D, Wolfson M, et al. Pegloticase immunogenicity: the relationship between efficacy and antibody development in patients treated for refractory chronic gout. Arthritis Res Ther. 2014;16:R60.
Maini RN, Breedveld FC, Kalden JR, Smolen JS, Davis D, Macfarlane JD, et al. Therapeutic efficacy of multiple intravenous infusions of anti-tumor necrosis factor alpha monoclonal antibody combined with low-dose weekly methotrexate in rheumatoid arthritis. Arthritis Rheum. 1998;41:1552-63.
Masri K, Winterling K, LaMoreaux B. Leflunomide co-therapy with pegloticase in uncontrolled gout. Ann Rheum Dis. 2020;79:450.
Mikuls T. R., Farrar J. T., Bilker W. B., Fernandes S., Schumacher H. R., Jr., Saag K. G. Gout epidemiology:results from the UK General Practice Research Database, 1990-1999. Ann Rheum Dis. 2005;64(2):267-72.
Nozue T, Yamamoto S, Tohyama S, Fukui K, Umezawa S, Onishi Y, et al. Correlations between serum uric acid and coronary atherosclerosis before and during statin therapy. Coron Art Dis. 2014;25:343-8.
Pan A, Teng GG, Yuan JM, Koh WP. Bidirectional association between self-reported hypertension and gout: the Singapore Chinese Health Study. PLoS One. 2015;10:e0141749.
Pan A, Teng GG, Yuan JM, Koh WP. Bidirectional association between diabetes and gout: the Singapore Chinese Health Study. Sci Rep. 2016;6:25766.
Park JJ, Roudier MP, Soman D, Mokadam NA, Simkin PA. Prevalence of birefringent crystals in cardiac and prostatic tissues, an observational study. BMJ Open. 2014;4:e005308.
Rainey H, Baraf HSB, Yeo A, Lipsky P. Companion immunosuppression with azathioprine increases the frequency of persistent responsiveness to pegloticase in patients with chronic refractory gout. Ann Rheum Dis. 2020;79:438.
Richette P, Doherty M, Pascual E, Barskova V, Becce F, Castaneda-Sanabria J, et al. 2016 updated EULAR evidence-based recommendations for the management of gout. Ann Rheum Dis. 2017;76:29-42.
Riedel AA, Nelson M, Joseph-Ridge N, Wallace K, MacDonald P, Becker M. Compliance with allopurinol therapy among managed care enrollees with gout: a retrospective analysis of administrative claims. J Rheumatol. 2004;31:1575-81.
Roddy Edward, Doherty Michael. Gout. Epidemiology of gout. Arthritis Research & Therapy. 2010;12(6).
Roughley MJ, Belcher J, Mallen CD, Roddy E. Gout and risk of chronic kidney disease and nephrolithiasis: meta-analysis of observational studies. Arthritis Res Ther. 2015;17:90.
Saag K. G., Choi H. Epidemiology, risk factors, and lifestyle modifications for gout. Arthritis Res Ther. 2006;8 Suppl 1:S2.
Sattui S. E., Singh J. A., Gaffo A. L. Comorbidities in patients with crystal diseases and hyperuricemia. Rheum Dis Clin North Am. 2014;40(2):251-78.
Schlesinger, Naomi, et al. "Canakinumab reduces the risk of acute gouty arthritis flares during initiation of allopurinol treatment: results of a double-blind, randomised study." Annals of the Rheumatic Diseases 70.7 (2011): 1264-1271.
Singh J. A., Strand V. Gout is associated with more comorbidities, poorer health-related quality of life and higher healthcare utilisation in US veterans. Ann Rheum Dis. 2008;67(9):1310-6.
Sundy JS, Baraf HS, Yood RA, Edwards NL, Gutierrez-Urena SR, Treadwell EL, et al. Efficacy and tolerability of pegloticase for the treatment of chronic gout in patients refractory to conventional treatment: two randomized controlled trials. JAMA. 2011;306:711-20.
Sundy, John S., et al. "Reduction of plasma urate levels following treatment with multiple doses of pegloticase (polyethylene glycol—conjugated uricase) in patients with treatment-failure gout: results of a phase II randomized study." Arthritis & Rheumatism 58.9 (2008): 2882-2891.
Tamariz L, Hernandez F, Bush A, Palacio A, Hare JM. Association between serum uric acid and atrial fibrillation: a systematic review and meta-analysis. Heart Rhythm. 2014;11:1102-8.
Weisman MH, Moreland LW, Furst DE, Weinblatt ME, Keystone EC, Paulus HE, et al. Efficacy, pharmacokinetic, and safety assessment of adalimumab, a fully human anti-tumor necrosis factor-alpha monoclonal antibody, in adults with rheumatoid arthritis receiving concomitant methotrexate: a pilot study. Clin Ther. 2003;25:1700-21.
Wertheimer Albert, Morlock Robert, Becker Michael A. A Revised Estimate of the Burden of Illness of Gout. Current Therapeutic Research. 2013;75:1-4.
Woodworth T, Furst DE, Alten R, Bingham CO 3rd, Yocum D, Sloan V, et al. Standardizing assessment and reporting of adverse effects in rheumatology clinical trials II: the rheumatology common toxicity criteria v.2.0. J Rheumatol. 2007;34:1401-14.
Yu KH, Kuo CF, Luo SF, See LC, Chou IJ, Chang HC, et al. Risk of end-stage renal disease associated with gout: a nationwide population study. Arthritis Res Ther. 2012;14:R83.
Zhao G, Huang L, Song M, Song Y. Baseline serum uric acid level as a predictor of cardiovascular disease related mortality and all-cause mortality: a meta-analysis of prospective studies. Atherosclerosis. 2013;231:61-8.
Zhu Y., Pandya B. J., Choi H. K. Prevalence of gout and hyperuricemia in the US general population: the National Health and Nutrition Examination Survey 2007-2008. Arthritis Rheum. 2011;63(10):3136-41.
Senter, Peter D., et al. "Generation of 5-fluorouracil from 5-fluorocytosine by monoclonal antibody-cytosine deaminase conjugates." Bioconjugate chemistry 2.6 (1991): 447-451.
Bagshawe, K. D. "Towards generating cytotoxic agents at cancer sites. The First Bagshawe Lecture." Br. J. Cancer 60 (1989): 275-281.
Bagshawe, K. D., et al. "A cytotoxic agent can be generated selectively at cancer sites." British journal of cancer 58.6 (1988): 700-703.
Senter, Peter D., et al. "Generation of cytotoxic agents by targeted enzymes." Bioconjugate chemistry 4.1 (1993): 3-9.
Battelli, M. G., et al. "T lymphocyte killing by a xanthine-oxidase-containing immunotoxin." Cancer Immunology, Immunotherapy 35.6 (1992): 421-425.
Pietersz, Geoffrey A., and Ian FC McKenzie. "Antibody conjugates for the treatment of cancer." Immunological reviews 129.1 (1992): 57-80.
Roffler, Steven R., et al. "Anti-neoplastic glucuronide prodrug treatment of human tumor cells targeted with a monoclonal antibody-enzyme conjugate." Biochemical pharmacology 42.10 (1991): 2062-2065.
Hughes, Brenda J., et al. "Monoclonal antibody targeting of liposomes to mouse lung in vivo." Cancer research 49.22 (1989): 6214-6220.
Litzinger, David C., and Leaf Huang. "Biodistribution and immunotargetability of ganglioside-stabilized dioleoylphosphatidylethanolamine liposomes." Biochimica et Biophysica Acta (BBA)-Biomembranes 1104.1 (1992): 179-187.
Brown, Valerie I., and Mark I. Greene. "Molecular and cellular mechanisms of receptor-mediated endocytosis." DNA and cell biology 10.6 (1991): 399-409.
Handbook of Monoclonal Antibodies, Ferrone et al., eds., Noges Publications, Park Ridge, N.J., (1985) ch. 22 and pp. 303-357.
Smith et al., Antibodies in Human Diagnosis and Therapy, Haber et al., eds., Raven Press, New York (1977) pp. 365-389.
Notice of Allowance received in connection with U.S. Appl. No. 18/409,450, dated Nov. 13, 2024, 9 pages.

(56) References Cited

OTHER PUBLICATIONS

International Preliminary Report on Patentability issued for Application No. PCT/US2023/079369, dated May 22, 2025.
U.S. Patent and Trademark Office. Final office action. Issued in U.S. Appl. No. 18/409,450. Jul. 15, 2024. 85 pages.

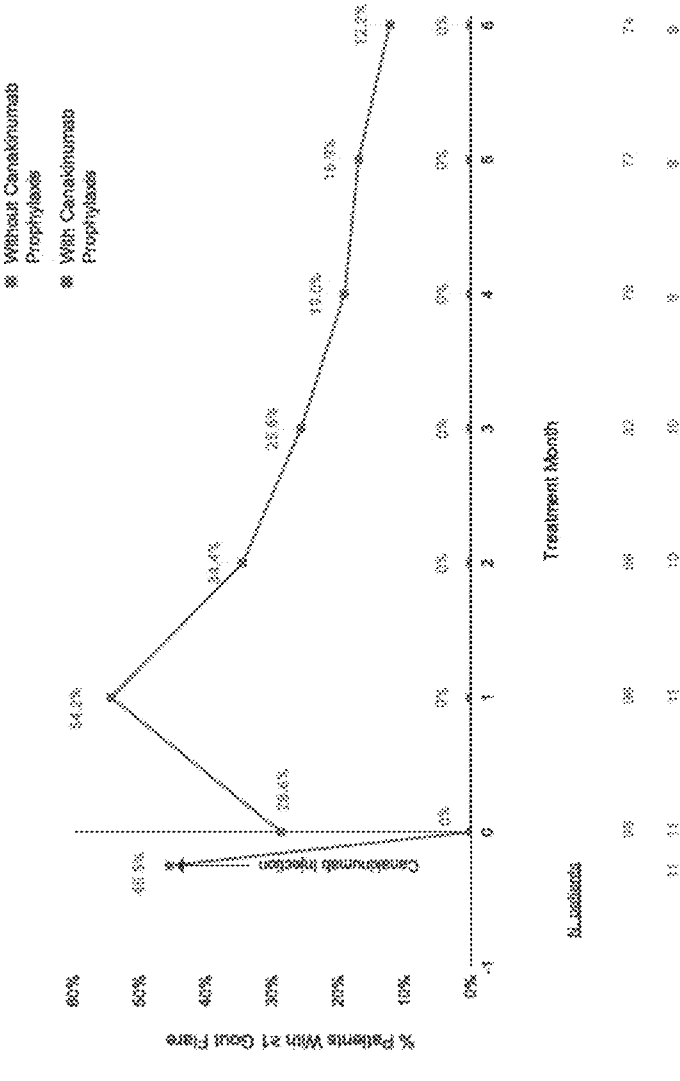
Acute Gout Flare During Pegloticase + MTX Treatment
Without Canakinumab Prophylaxis
With Canakinumab Prophylaxis
Canakinumab Injection
% Patients With ≥1 Gout Flare
Treatment Month

GOUT FLARE PREVENTION METHODS USING IL-1β BLOCKERS

I. CROSS REFERENCE TO RELATED APPLICATIONS

This application claims the benefit of U.S. Provisional Application No. 63/517,598, filed on Aug. 3, 2023, and U.S. Provisional Application No. 63/424,621, filed on Nov. 11, 2022, applications which are incorporated herein by reference in their entireties.

II. REFERENCE TO SEQUENCE LISTING

The sequence listing submitted on Nov. 10, 2023, as an .XML file entitled “11608-003US1.XML” created on Nov. 9, 2023, and having a file size of 2,006 bytes is hereby incorporated by reference pursuant to 37 C.F.R. § 1.52(e)(5).

III. BACKGROUND

1. Gout is a common, inflammatory arthritis caused by monosodium urate deposition in the setting of chronically elevated serum urate levels (SU>6 mg/dL). Monosodium urate crystals cause chronic systemic inflammation, even between acute gout flares. In the past, gout patients have been treated with pegloticase, either alone or with methotrexate. A methotrexate/pegloticase combination therapy has shown a higher responder rate. The combination therapy approach has been improved further by treating gout patients with methotrexate prior to treating with either pegloticase or a combination of methotrexate and pegloticase. Often, the treatment course is at least one, but often two weeks of methotrexate, followed by a combination of methotrexate and pegloticase. However, despite the improvements in patient outcomes, 54% people undergoing treatment for gout often experience gout flares. Acute gout flares are a known result of urate-lowering in gout patients and are the most common adverse event in patients treated with pegloticase. What is needed are new methods of treating gout patients that does not suffer from gout flares.

IV. SUMMARY

2. Disclosed are methods and compositions related to the treatment of gout and/or gout flares.

3. In one aspect, disclosed herein are methods of inhibiting, reducing, decreasing, ameliorating, and/or preventing gout flares in a patient in need thereof, comprising administering a gout flare-ameliorating amount of at least one IL-1β inhibitor (such as, for example, canakinumab (Ilaris)) prior to the occurrence of gout flares. In some aspects, the method does not include the administration of a corticosteroid.

4. Also disclosed herein are methods of inhibiting, reducing, decreasing, ameliorating, and/or preventing gout flares of any preceding aspect, wherein the at least one IL-1β inhibitor is administered prior to (such as, for example 1, 2, 3, or 4 weeks before), simultaneously to, contemporaneously with, or subsequent to (such as, for example 1, 2, 3, or 4 weeks after) administration of an immunomodulatory agent (such as, for example, methotrexate).

5. In one aspect, disclosed herein are methods of inhibiting, reducing, decreasing, ameliorating, and/or preventing gout flares of any preceding aspect, further comprising administering a uricase (such as, for example, pegloticase (KRYSTEXXA®)) to the patient. In one aspect, the uricase is administered concurrently with or after administration of the IL-1β inhibitor.

6. Also disclosed herein are methods of inhibiting, reducing, decreasing, ameliorating, and/or preventing gout flares of any preceding aspect, wherein the immunomodulatory agent (such as, for example methotrexate) is administered for at least 4 weeks prior; wherein the at least one dose of an IL-1β inhibitor (such as, for example, canakinumab) is administered either alone or in combination with the immunomodulatory agent; and wherein the uricase (such as, for example, pegloticase) is administered alone or concurrently with, including in a composition with, immunomodulatory agent and/or the IL-1β inhibitor. For example, disclosed herein are methods of inhibiting, reducing, decreasing, ameliorating, and/or preventing gout flares of any preceding aspect, wherein the immunomodulatory agent (such as, for example methotrexate) is administered for at least 4 weeks prior to administration of the uricase (such as, for example, pegloticase); wherein the at least one dose of an IL-1β inhibitor (such as, for example, canakinumab) is administered either alone or in combination with the immunomodulatory agent three weeks after first administration of the immunomodulatory agent and seven days before administration of the uricase; and wherein the uricase is administered alone or in combination with the immunomodulator agent. In one aspect, the immunomodulatory agent is administered weekly for at least three weeks, the IL-1β inhibitor is administered once, and the uricase is administered for at least bi-weekly. In some aspect, the immunomodulatory agent continues to be administered weekly after administration of the IL-1β inhibitor. In some aspects, the first administration of the immunomodulatory agent occurs before administration of the IL-1β inhibitor. In some aspects, the first administration of the immunomodulatory agent occurs after administration of the IL-1β inhibitor. In some aspects, the IL-1β inhibitor is administered prior to or concurrently with any administration of the uricase.

7. Also disclosed herein are treatment regimens for inhibiting gout flares in a patient in need thereof, comprising: a) administering an immunomodulatory agent (such as, for example methotrexate), weekly for at least four weeks; b) administering at least one dose of an IL-1β inhibitor (such as, for example canakinumab (Ilaris)) either alone or in combination with the immunomodulatory agent; and c) administering a uricase (such as, for example, pegloticase (KRYSTEXXA®), either alone or in combination with immunomodulatory agent (such as, for example methotrexate), for a period of time to control gout. In some aspects, the treatment regimen does not include the administration of a corticosteroid 8. In one aspect, disclosed herein are treatment regimens of any preceding aspect, wherein immunomodulatory agent is administered weekly for at least three weeks; the IL-1β inhibitor is administered once three weeks after the first administration of the immunomodulatory agent; and the uricase is administered for at least bi-weekly. In some aspects the administration of the IL-1β inhibitor occurs three weeks after the first administration of the immunomodulatory agent. In some aspect, the immunomodulatory agent continues to be administered weekly after administration of the IL-1β inhibitor. In some aspects, the first administration of the immunomodulatory agent occurs before administration of the IL-1β inhibitor. In some aspects, the first administration of the immunomodulatory agent occurs after administration of the IL-1β inhibitor. In some aspects, the IL-1β inhibitor is administered prior to or concurrently with any administration of the uricase.

9. In some aspects, the immunomodulatory agent continues to be administered weekly after administration of the IL-1β inhibitor.

10. Also disclosed herein are treatment regimens of any preceding aspect, wherein the first administration of the immunomodulatory agent occurs after administration of the IL-1β inhibitor.

11. In one aspect, disclosed herein are treatment regimens of any preceding aspect, wherein the IL-1β inhibitor is administered prior to any administration of the uricase.

12. Also disclosed herein are treatment regimens of any preceding aspect, wherein the IL-1β inhibitor is administered concurrently with the first administration the uricase.

V. BRIEF DESCRIPTION OF THE DRAWINGS

13. The accompanying drawings, which are incorporated in and constitute a part of this specification, illustrate several embodiments and together with the description illustrate the disclosed compositions and methods.

14. FIG. 1 shows the percentage of patients experiencing ≥1 acute gout flare by month. Flares required ≥3 of 4 criteria (patient-defined gout flare, pain at rest score ≥3 on 0-10 scale, ≥1 swollen joint, ≥1 tender joint). Canakinumab injection was administered at day −7±2. Canakinumab flare data represents the prior 3-week MTX run-in period before the injection and month 0 flares from canakinumab administration to first pegloticase infusion. Data from MIRROR RCT (active arm) provided for non-statistical comparison only. 3 Month 0 represents the 4-week MTX run-in period.

VI. DETAILED DESCRIPTION

15. Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

16. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

17. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

18. In this specification and in the claims which follow, reference will be made to a number of terms which shall be defined to have the following meanings:

19. "Optional" or "optionally" means that the subsequently described event or circumstance may or may not occur, and that the description includes instances where said event or circumstance occurs and instances where it does not.

20. An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

21. A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

22. "Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

23. By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

24. By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

25. The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

26. The term "therapeutically effective" refers to the amount of the composition used is of sufficient quantity to ameliorate one or more causes or symptoms of a disease or disorder. Such amelioration only requires a reduction or alteration, not necessarily elimination.

27. The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

28. "Biocompatible" generally refers to a material and any metabolites or degradation products thereof that are generally non-toxic to the recipient and do not cause significant adverse effects to the subject.

29. "Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

30. A "control" is an alternative subject or sample used in an experiment for comparison purposes. A control can be "positive" or "negative."

31. "Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

32. A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

33. "Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

34. "Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

35. "Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

36. "Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

37. Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods to Prevent Gout Flares

38. Gout effects approximately 4% of the US population, it is the most common form of inflammatory arthritis in men, and is associated with decreased quality of life. The frequency of gout is increasing worldwide, with prevalence rate estimated to be as high as 7% in older men. It is estimated that up to 400,000 persons in the United States experience chronic refractory gout, characterized by ongoing symptoms of active disease and a failure of control/maintain serum urate less than 6 mg/dL with conventional xanthene oxidase inhibitors (i.e. Allopurinol and febuxostat) and uricosuric agents (i.e. Probenecid). These patients often have significant, disabling urate deposits in soft tissue and bone known as tophi.

39. Pegloticase, a recombinant modified mammalian urate oxidase (uricase) which is a class of protein drug that also includes rasburicase. Pegloticase is a pegylated form of urizase and is approved by the food and drug administration to be used in combination with methotrexate in patients with uncontrolled gout. Pegloticase is very efficacious at reducing serum uric acid and improving clinical signs and symptoms of gout such as tophi size. However, initiation of pegloticase has been associated with high rates of gout flares, a significant cause of pain and reduction in quality of life, and a major cause of discontinuation of pegloticase treatment.

40. Gout flares which occur with initiation of urate lowering therapy, result from mobilization of uric acid crystals, which is thought to react with macrophages through an IL-1 mediated mechanism. Prophylaxis with corticosteroids, NSAIDs, and colchicine have been used in the past to help prevent or decrease the intensity and number of flares with limited success. Immunomodulation with methotrexate and pegloticase created a paradigm shift in gout management with improved safety and efficacy. Despite pre-infusion corticosteroids, 54% of patients still experienced flares at month 1. Acute gout flares are a known result of urate-lowering in gout patients and are the most common adverse event in patients treated with pegloticase.

41. Canakinumab is a fully human anti-interleukin 1β monoclonal antibody currently approved by the FDA for the treatment of periodic fever syndromes and active systemic juvenile idiopathic arthritis (SJIA). In Europe canakinumab is also approved for adult onset Still's disease and for the symptomatic treatment of adult patients with frequent gouty attacks (at least 3 attacks in the previous 12 months) in whom non-steroidal anti-inflammatory drugs (NSAIDs) and colchicine are contraindicated, are not tolerated, or do no provide an adequate response, and in whom repeated courses of corticosteroids are not appropriate. A single dose of canakinumab ≥50 mg provided superior prophylaxis against flares compared to colchicine when initiating treatment with allopurinol; however; its use as prophylaxis with pegloticase has not been studied.

42. As shown herein, Canakinumab prophylaxis without corticosteroids (suggesting an IL-1 mechanism) prevented gout flares in 100% of treated patients. These findings are especially noteworthy as the prevention of gout flares caused by initiation of pegloticase with methotrexate by canakinumab prophylaxis is done without the use of pre-infusion corticosteroids with safety and efficacy unchanged. Accordingly, in one aspect, the present disclosure provides gout flare inhibition, reduction, amelioration, and/or prevention methods using IL-1β inhibitors. In particular, the IL-1β inhibitor canakinumab can be utilized in the present methods. Accordingly, disclosed herein are methods of inhibiting, reducing, decreasing, ameliorating, and/or preventing gout flares in a patient in need thereof, comprising administering a gout flare-ameliorating amount of at least one IL-1β inhibitor (such as, for example, canakinumab (Ilaris)) prior to the occurrence of gout flares. In some aspects, the method does not include the administration of a corticosteroid. In one aspect, disclosed herein are methods of inhibiting, reducing, decreasing, ameliorating, and/or preventing gout flares, further comprising administering a uricase (such as, for example, pegloticase (KRYSTEXXA®)) and an immunomodulator agent to the patient. In one aspect, the uricase is administered concurrently with or after administration of the IL-1β inhibitor.

43. The IL-1β inhibitors useful in the present methods and treatment regimens include those described in U.S. Pat. No. 8,524,667, the disclosure of which is specifically incorporated by reference. Examples of IL-1b inhibitors include, but are not limited to anakinra, canakinumab, gevokizumab, LY2189102, CYT013, soluble IL-1 receptor II (sIL-1RII), and rilonacept. Canakinumab is a human monoclonal anti-human IL-1β antibody of the IgG1/K isotype. Canakinumab binds to human IL1β and neutralizes its activity by blocking its interaction with IL-1 receptors, but it does not bind IL-1α or IL-1 receptor antagonist (IL-1ra).

44. Canakinumab is a recombinant, human anti-human-IL-1β monoclonal antibody that belongs to the IgG1/κ isotype subclass. It is expressed in a murine Sp2/0-Ag14 cell line and comprised of two 447- (or 448-) residue heavy chains and two 214-residue light chains, with a molecular mass of 145157 Daltons when deglycosylated. Both heavy chains of canakinumab contain oligosaccharide chains linked to the protein backbone at asparagine 298 (Asn 298). The biological activity of canakinumab is measured by comparing its inhibition of IL-1β-dependent expression of the reporter gene luciferase to that of a canakinumab internal reference standard, using a stably transfected cell line. ILARIS Injection ILARIS (canakinumab) Injection is supplied as a sterile, preservative-free, clear to opalescent, colorless to slightly brownish-yellow solution for subcutaneous injection in a single-dose, glass vial with coated stopper and aluminum flip-off cap. Each vial delivers 1 mL containing 150 mg canakinumab, L-histidine (2.1 mg), L-histidine HCl monohydrate (1.3 mg), mannitol (49.2 mg), polysorbate 80 (0.4 mg), and Sterile Water for Injection.

45. For all indications disclosed herein this description (Indications of the inventions), the appropriate dosage will, of course, vary depending upon, for example, the particular IL-1β Compounds, e.g. the Antibodies to be employed, the host, the mode of administration and the nature and severity of the condition being treated. However, in prophylactic use, satisfactory results are generally indicated to be obtained at dosages from about 0.05 mg to about 10 mg per kilogram body weight more usually from about 0.1 mg to about 5 mg per kilogram body weight. Antibody of the Invention is conveniently administered parenterally, intravenously, e.g. into the antecubital or other peripheral vein, intramuscularly, or subcutaneously.

46. The recommended dose of interleukin-10 (IL-1β) inhibitor for prevention of gout flare-ups in gout patients is based on body weight. For patients with body weight less than or equal to 40 kg, the recommended dose is 2 mg/kg administered every 4 weeks. The dose can be increased to 4 mg/kg every 4 weeks if the clinical response is not adequate. For patients with body weight greater than 40 kg, the recommended dose is 150 mg administered every 4 weeks. The dose can be increased to 300 mg every 4 weeks if the clinical response is not adequate. In one aspect, it is understood and herein contemplated the IL-1β inhibitor can be administered at any therapeutically effective amount sufficient to inhibit, reduce, ameliorate, decrease and/or prevent gout flares. In some embodiments, at least about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 mg of the IL-1β inhibitor is administered to the subject. The IL-1β inhibitor can be administered as a single dose or multiple doses. For example, the IL-1β inhibitor can be administered 1, 2, 3, 4, 5, 6, 7, 8, 9, 10 or more times. In some aspects, only one dose of the IL-1β inhibitor is administered to the patient.

47. In some embodiments, the methods of inhibiting, reducing, decreasing, ameliorating, and/or preventing gout flares further comprise administering to the subject at least one immunomodulatory agent, wherein the at least one immunomodulatory agent comprises methotrexate, mycophenolate, azathioprine, leflunomide, pomalidomide, lenalidomide, sulfasalazine diphenhydramine, cetirizine, famotidine, montelukast, acetaminophen, methylprednisolone, folic acid, or prednisone. Thus, also disclosed herein are methods to inhibit, reduce, decrease, ameliorate, and/or prevent gout flares, wherein the at least one IL-1β inhibitor is administered simultaneously to, contemporaneously with, or subsequently to (such as, for example 1, 2, 3, or 4 weeks before or after) administration of an immunomodulatory agent (such as, for example, methotrexate). It is understood and herein contemplated that timing and duration of the immunomodulatory treatment can depend on the choice of immunomodulatory agent used. For example, where methotrexate is used an immunomodulatory agent, the method can comprise 4 weeks of pretreatment before administration of a uricase. If mycophenolate is used, the pretreatment can be two weeks, and if leflunomide is used, no pretreatment is needed and it maybe given the same day. Administration of the immunomodulatory agent can occur for a time period sufficient to reduce gout flares such as, for example, at least once every 1, 2, 3, 4,5 6, 7 days, 2, 3, 4, 5, 6, 7, or 8 weeks. Also disclosed herein are methods of inhibiting, reducing, decreasing, ameliorating, and/or preventing gout flares, wherein the at least one IL-1β inhibitor is administered prior to (such as, for example 1, 2, 3, 4, 5, 6, 7, 8, 9, 10, 11, 12, 13, 14 days, 3, or 4 weeks before), simultaneously to, contemporaneously with, or subsequent to (such as, for example 1, 2, 3, 4, 5, 6, 7, 8, 9, 10, 11, 12, 13, 14 days, 3, or 4 weeks after) administration of an immunomodulatory agent (such as, for example, methotrexate).

48. As noted throughout this disclosure the treatment of gout can often utilize the use of uricase. It should be understood and herein contemplated that "urate oxidase" or "uricase" is an enzyme that catalyzes the oxidation of highly insoluble uric acid to 5-hydroxyisourate. The uricase disclosed in the invention can be used for treating gouty arthropathy. In some embodiments, the uricase of any preceding comprises rasburicase or Pegloticase. Pegloticase is a recombinant porcine-like uricase drug indicated for the treatment of severe, treatment-refractory, chronic gout. It is a tetrameric protein composed of four identical chains of about 300 amino acid each. Sequence of one chain can be TYKKNDEVEFVRTGYGKDMIKVL-HIQRDGKYHSIKEVATTVQLTLSSKKDYLHGDNSD VIPTDTIKNTVNVLAKFKGIKSI-ETFAVTICEHFLSSFKHVIRAQVYVEEVPWKR-FEKNGV KHVHAFIYTPTGTHFCE-VEQIRNGPPVIHSGIKDLKVLKTTQSGFEGFIKDQFTT LPEVKD RCFATQVYCKWRYHQGRDVD-FEATWDTVRSIVLQKFAGPYDKGEYSPSVQKTLYDIQ VLTLGQVPEIEDMEISLPNIHYLNIDMSKMGLIN-KEEVLLPLDNPYGKITGTVKRKLSSRL (SEQ ID NO: 1).

49. In some embodiments, the term "uricase" used herein also refers to any variants, derivatives, or prodrugs of uricase, including, for example, Rasburicase or poly(ethylene glycol) (PEG) conjugate of recombinant porcine-like uricase (PEG-uricase). Thus, in one aspect, disclosed herein are methods to inhibit, reduce, decrease, ameliorate, and/or prevent gout flares of any preceding aspect, further comprising administering a uricase (such as, for example, pegloticase) to the patient.

50. Administration of the uricase can occur at the dosing amounts and frequency already approved by the FDA for the treatment of gout. In one aspect, administration of the uricase occurs at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 days, 6, 7, 8, 9, 10, 11 or 12 weeks after the first administration of the immunomodulatory agent and/or the IL-1β inhibitor. The administration of the uricase can occur at least once every 1, 2, 3, 4, 5, 6, 7 days, 2, 3, 4, 5, 6, 7, or 8 weeks. In some aspects, the uricase is administered after administration of the immunomodulatory agent, but prior to, simultaneously with, or contemporaneously with the IL-1β inhibitor.

51. Also disclosed herein are methods of inhibiting, reducing, decreasing, ameliorating, and/or preventing gout flares of any preceding aspect, wherein the immunomodulatory agent (such as, for example, methotrexate, mycophenolate, azathioprine, leflunomide, pomalidomide, lenalidomide, sulfasalazine diphenhydramine, cetirizine, famotidine, montelukast, acetaminophen, methylprednisolone, folic acid, or prednisone) is administered for at least 4 weeks prior; wherein the at least one dose of an IL-1β inhibitor (such as, for example, canakinumab) is administered either alone or in combination with the immunomodulatory agent; and wherein the uricase (such as, for example, pegloticase) is administered alone or concurrently with, including in a composition with, immunomodulatory agent and/or the IL-1β inhibitor. For example, disclosed herein are methods of inhibiting, reducing, decreasing, ameliorating, and/or preventing gout flares of any preceding aspect, wherein the immunomodulatory agent (such as, for example methotrexate) is administered for at least 4 weeks prior to administration of the uricase (such as, for example, pegloticase); wherein the at least one dose of an IL-1β inhibitor (such as, for example, canakinumab) is administered either alone or in combination with the immunomodulatory agent three weeks after first administration of the immunomodulatory agent and seven days before administration of the uricase; and wherein the uricase is administered alone or in combination with the immunomodulator agent. In one aspect, the immunomodulatory agent is administered weekly for at least three weeks, the IL-1β inhibitor is administered once, and the uricase is administered for at least bi-weekly. In some aspect, the immunomodulatory agent continues to be administered weekly after administration of the IL-1β inhibitor. In some aspects, the first administration of the immunomodulatory agent occurs before administration of the IL-1β inhibitor. In some aspects, the first administration of the immunomodulatory agent occurs after administration of the IL-1β inhibitor. In some aspects, the IL-1β inhibitor is administered prior to or concurrently with any administration of the uricase.

52. In one aspect, disclosed herein are methods to inhibit, decrease, reduce, ameliorate, and/or prevent gout flares, wherein: immunomodulatory agent is administered weekly for at least three weeks, the IL-1β inhibitor is administered once three weeks after the first administration of the immunomodulatory agent, and the uricase is administered for at least bi-weekly.

53. Additionally, the present disclosure provides treatment regimens for the inhibition, reduction, amelioration, and/or prevention of gout flares comprising the administration of an immunomodulatory agent, an IL-1β inhibitor, and a uricase. Thus, disclosed herein are treatment regimens for inhibiting gout flares in a patient in need thereof, comprising: a) administering an immunomodulatory agent (such as, for example methotrexate), weekly; b) administering at least one dose of an IL-1β inhibitor (such as, for example canakinumab (Ilaris)) either alone or in combination with the immunomodulatory agent; and c) administering a uricase (such as, for example, pegloticase (KRYSTEXXA®), either alone or in combination with immunomodulatory agent (such as, for example methotrexate), for a period of time to control gout.

54. As noted above, timing and duration of the immunomodulatory treatment can depend on the choice of immunomodulatory agent used. For example, where methotrexate is used an immunomodulatory agent, the method can comprise 4 weeks of pretreatment before administration of a uricase. If mycophenolate is used, the pretreatment can be two weeks, and if leflunomide is used, no pretreatment is needed and it maybe given the same day. Thus, in one example, disclosed herein are treatment regimens for inhibiting gout flares in a patient in need thereof, comprising: a) administering an immunomodulatory agent (such as, for example methotrexate), weekly for at least four weeks; b) administering at least one dose of an IL-1β inhibitor (such as, for example canakinumab (Ilaris)) either alone or in combination with the immunomodulatory agent; and c) administering a uricase (such as, for example, pegloticase (KRYSTEXXA®), either alone or in combination with immunomodulatory agent (such as, for example methotrexate), for a period of time to control gout. In some aspects, the treatment regimen does not include the administration of a corticosteroid 55. In one aspect, disclosed herein are treatment regimens of any preceding aspect, wherein immunomodulatory agent is administered weekly for at least three weeks; the IL-1β inhibitor is administered once three weeks after the first administration of the immunomodulatory agent; and the uricase is administered for at least bi-weekly. In some aspects the administration of the IL-1β inhibitor occurs three weeks after the first administration of the immunomodulatory agent. In some aspect, the immunomodulatory agent continues to be administered weekly after administration of the IL-1β inhibitor. In some aspects, the first administration of the immunomodulatory agent occurs before administration of the IL-1β inhibitor. In some aspects, the first administration of the immunomodulatory agent occurs after administration of the IL-1β inhibitor. In some aspects, the IL-1β inhibitor is administered prior to or concurrently with any administration of the uricase.

56. In one aspect, disclosed herein are treatment regimens, wherein the IL-1β inhibitor is administered prior to any administration of the uricase.

57. Also disclosed herein are treatment regimens, wherein the IL-1β inhibitor is administered concurrently with the first administration the uricase.

58. In some aspects, the following exclusive and sequential administration is claimed: administration of immunomodulatory agent (such as, for example, methotrexate or any other immunomodulatory agent disclosed herein including, but not limited to mycophenolate, azathioprine, leflunomide, pomalidomide, lenalidomide, sulfasalazine diphenhydramine, cetirizine, famotidine, montelukast, acetaminophen, methylprednisolone, folic acid, or prednisone), followed by administration of IL-1β inhibitor (such as, for example, canakinumab), followed by administration of a uricase (such as, for example, pegloticase). In one aspect, the immunomodulatory agent (such as, for example, methotrexate) is administered weekly for three weeks. On the third week of administration of immunomodulatory agent (such as, for example, methotrexate), the IL-1β inhibitor (such as, for example, canakinumab). One week after administration of the IL-1β inhibitor (such as, for example, canakinumab) and the third weekly administration of the immunomodulatory agent (such as, for example, methotrexate), the uricase is administered. Administration of the immunomodulatory agent can continue as at least a weekly, bi-weekly, monthly, or bi-monthly dose or stop after administration of the uricase. Similarly, administration of the IL-1β inhibitor can stop following administration of the uricase or continue at a periodic rate such as at least once every 1, 2, 3, 4, 5, 6, 7 days, 2, 3, 4, 5, 6, 7, 8, 9, 10, 11, 12 weeks, or 3, 4, 5, 6, 7, 8, 9, 10, 11, 12 months. Administration of the uricase (such as, for example, pegloticase) can occur at the FDA approved concentration and/or rate or at rates and therapeutic amounts less than the FDA approved amount due to synergistic effects with the administration of the IL-1β inhibitor.

59. In one embodiment, methotrexate is administered to a gout patient for a time period selected from the group consisting of: at least about one week, at least about two weeks, at least about three weeks, and at least about three weeks, followed by administration of the IL-1β inhibitor for a time period sufficient to reduce gout flares, followed by administration of pegloticase for a time period necessary to treat or control gout.

60. Administration of canakinumab (Ilaris) solution can include:

61. STEP 1: ILARIS solution has a concentration of 150 mg/mL. The solution should be essentially free from particulates, clear to opalescent, colorless to slightly brownish-yellow tint. If the solution has a distinctly brown discoloration, is highly opalescent or contains visible particles, do not use. STEP 2: Using a sterile 1-mL syringe and 18-gauge×2" needle, carefully withdraw the required volume depending on the dose to be administered and subcutaneously inject using a 27-gauge×0.5" needle. Injection into scar tissue should be avoided as this may result in insufficient exposure to ILARIS. Discard unused product or waste material in accordance with the local requirements. 3

62. DOSAGE FORMS AND STRENGTHS Injection: 150 mg/mL solution in single-dose vials. The solution is a clear to slightly opalescent, colorless to a slightly brownish yellow tint.

63. In yet another embodiment, the invention concerns a surprising frequency of dosing for therapeutic uses, i.e. the treatment schedule with IL-1beta Compounds, preferably IL-1beta antibodies, more preferably ACZ885 (at a typical dose, e.g. between about 0.1 mg to about 50 mg, more preferably between 0.5 mg to 20 mg, even more preferably from 1 mg to 10 mg, of ACZ885 per kg body weight of the patient) may be once every week or less frequently, more preferably once every 2 weeks or less frequently, more preferably once every 3 weeks or less frequently, more preferably once every month or less frequently, more preferably once every 2 months or less frequently, more preferably once every 3 months or less frequently, even more preferably once every 4 months or less frequently, even more preferably once every 5 months or less frequently, or even more preferably once every 6 months or less frequently. Most preferred is once every month.

64. Administration of the disclosed immunomodulatory agents, IL-1b inhibitors, and uricases can occur via any route of administration known in the art, including, but not limited to topically (including ophthalmically, vaginally, rectally, intranasally), orally, intracavity, transdermally, by inhalation, or parenterally, for example by intravenous drip, subcutaneous, intraperitoneal or intramuscular injection.

65. Pharmaceutical compositions of the invention may be manufactured in conventional manner A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

66. It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

1. Pharmaceutical Carriers/Delivery of Pharmaceutical Products

67. As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

68. The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

69. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

70. The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

a) Pharmaceutically Acceptable Carriers

71. The compositions, including antibodies, can be used therapeutically in combination with a pharmaceutically acceptable carrier.

72. Suitable carriers and their formulations are described in Remington: The Science and Practice of Pharmacy (19th ed.) ed. A. R. Gennaro, Mack Publishing Company, Easton, P A 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

73. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

74. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

75. The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

76. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

77. Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

78. Compositions for oral administration include powders or granules, suspensions or solutions in water or non-aqueous media, capsules, sachets, or tablets. Thickeners, flavorings, diluents, emulsifiers, dispersing aids or binders may be desirable.

79. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines b) Therapeutic Uses 80. Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

C. Examples

81. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Study population

82. Patients with uncontrolled gout aged 18-65 years were considered for trial enrollment. Patients were said to have uncontrolled gout if their SU level was ≥6 mg/dL at screening and at least one of the following was true: they were unable to maintain SU<6 mg/dL on an oral ULT, they had an intolerance to their current ULT, or tophaceous deposits that limited patient functionality were present (detected clinically or with dual-energy computed tomography [DECT]). The key exclusion criteria included serious acute bacterial infection <2 weeks prior to screening, severe chronic/recurrent bacterial infection, immunocompromised status, glucose-6-phosphate dehydrogenase (G6PD) deficiency (tested at screening), severe chronic renal impairment (glomerular filtration rate [GFR]<25 mL/min/1.73 $m^2$ or currently on dialysis), or liver disease (alanine aminotransferase [ALT] or aspartate aminotransferase [AST]>3 times upper limit).

b) Study Medications

83. All enrolled patients were scheduled to receive 4 weeks of oral methotrexate (15 mg/week, run-in period) followed by treatment with pegloticase. Patients can be administered an IL-1β inhibitor, specifically, canakinumab, according to appropriate protocols.

84 Canakinumab can be followed by both pegloticase (8 mg infusion every 2 weeks) and methotrexate (15 mg orally every week) for up to 52 weeks (treatment period). The methotrexate dose was chosen based on the enhancement of other biologics' durability when methotrexate was used as co-therapy, published rheumatology expert opinions, and study advisory board recommendations. The original protocol included a 24-week treatment period, but a protocol amendment extended the treatment period to 52 weeks. Patients also received 1 mg/day of oral folic acid during both the run-in and treatment periods. All patients were required to begin gout flare prophylaxis (colchicine, non-steroidal anti-inflammatory drugs [NSAIDs], and/or low-dose prednisone [≤10 mg/day] as chosen by the treating physician) at least 1 week prior to initiating pegloticase, continuing flare prophylaxis per American College of Rheumatology guidelines. When they did occur, flares were managed with NSAIDs, colchicine, corticosteroids, and intraarticular steroid injections at the treating physician's discretion.

85. Patients were administered standard IR prophylaxis prior to each pegloticase infusion. This included oral fexofenadine (60 or 180 mg) the day before and morning of infusion, acetaminophen (1000 mg) the morning of infusion, and intravenous glucocorticoid (200 mg hydrocortisone or 125 mg methylprednisolone) immediately prior to each infusion. An SU monitoring protocol was implemented to decrease the risk of IRs. Patients discontinued pegloticase+methotrexate co-therapy if they had two consecutive SU measurements above 6 mg/dL after week 2.

2. Example 2: Canakinumab Pretreatment to Reduce Flares in Gout Patients Receiving Pegloticase Plus Methotrexate Therapy 86. Pegloticase plus methotrexate (approved by FDA in July 2022) is effective at reducing signs/symptoms of uncontrolled gout. In the pivotal trial (MIRROR RCT) the most common adverse event was gout flares which occurred in 54% of patients at month 1 on combination pegloticase and methotrexate. The purpose of this study is to determine if canakinumab is effective for the prevention of gout flares in subjects scheduled to begin KRYSTEXXA® (KRY) (pegloticase) infusions in combination with methotrexate. The most common adverse event that occurs in patients being treated with KRY and methotrexate are gout flares which occurred in 54% of patients at month 1 in the MIRROR RCT. Herein we use canakinumab pretreatment (without corticosteroids, NSAIDs, or colchicine) to reduce the number of gout flares.

87 Canakinumab is the drug that is tested herein. It is currently approved by the FDA for the treatment of periodic fever syndromes and active systemic juvenile idiopathic arthritis (SJIA). However, Canakinumab is considered to be experimental in this study. Subjects scheduled (by their treating provider) to receive pegloticase (with methotrexate) receive a single 150 mg injection of subcutaneous canakinumab one week prior to the first scheduled pegloticase infusion. The combination of the drugs is experimental. As shown herein, 88. Subjects scheduled (by their treating provider) to receive pegloticase (with methotrexate) receive a single 150 mg injection of subcutaneous canakinumab one week prior to the first scheduled pegloticase infusion. At each infusion, subjects are assessed for gout flares. Canakinumab are provided by the study to subjects without charge. Pegloticase, methotrexate, and other medications are obtained through standard means (patient insurance, patient assistance, etc.) as ordered by treating provider. As shown herein, canakinumab reduces the risk of flares of gout during the initiation of allopurinol. It is assumed that mobilization of gout crystals at the initiation of therapy results in gout flares through the IL-1 inflammasome pathway. A goal of prophylaxis is to reduce the number of flares with initiation. Currently pretreatment with corticosteroids, NSAIDs, and colchicine are used, but are only partially effective in some patients. Herein canakinumab pretreatment (without corticosteroids, NSAIDs, or colchicine) is used to reduce the number of gout flares that occur with initiating pegloticase with methotrexate.

89. Seven days prior to administration of KRYSTEXXA® (pegloticase)(i.e., Day −7), patients receive a canakinumab 150 mg subcutaneous injection into the abdomen or anterior thigh. On the day of KRYSTEXXA® administration (i.e., Day 0), the blood pressure, respiratory rate, temperature, and heart rate of patients are measured and patients receive a first administration of KRYSTEXXA® delivered as an intravenous (i.v.) infusion. Every two weeks thereafter during the study (i.e., Day 14, Day 28, Day 42, Day 56, Day 72, Day 86, Day 98, Day 112, Day 126, Day 140, Day 154, Day 168; also called Week 2, Week 4, Week 6, Week 8, Week 10, Week 12, Week 14, Week 16, Week 18, Week 20, Week 22, Week 24) the blood pressure, respiratory rate, temperature, and heart rate of patients are measured and patients report any gout flares. Additionally, patients receive further administration of KRYSTEXXA® via intravenous infusion.

a) Material and Methods (1) Canakinumab

90 Canakinumab for Injection is supplied by Novartis Pharmaceuticals Corporation as a white, preservative-free, lyophilized powder in a sterile, single-dose, colorless, glass vial with coated stopper and aluminum flip-off cap. Reconstitution with 1 mL of Sterile Water for Injection is required prior to subcutaneous administration of the drug. The reconstituted canakinumab is a 150 mg/mL solution essentially free of particulates, clear to opalescent, and is colorless or may have a slightly brownish-yellow tint. A volume of up to 1 mL can be withdrawn for delivery of 150 mg canakinumab, L-histidine (2.8 mg), L-histidine HCl monohydrate (1.7 mg), polysorbate 80 (0.6 mg), sucrose (92.4 mg), and Sterile Water for Injection. All participants receive canakinumab 150 mg by subcutaneous injection at day −7.

(2) Preparation

91. STEP 1: Using aseptic technique, reconstitute each vial of ILARIS lyophilized powder by slowly injecting 1 mL of Sterile Water for Injection with a 1-mL syringe and an 18-gauge×2" needle. STEP 2: Swirl the vial slowly at an angle of about 45° for approximately 1 minute and allow to stand for 5 minutes. Do not shake. Then gently turn the vial upside down and back again ten times. Avoid touching the rubber stopper with your fingers. STEP 3: Allow to stand for about 15 minutes at room temperature. The reconstituted solution has a final concentration of 150 mg/mL. Do not shake. Do not use if particulate matter is present in the solution. Tap the side of the vial to remove any residual liquid from the stopper. The reconstituted solution should be clear to opalescent, colorless to a slightly brownish yellow tint, and essentially free from particulates. If the solution has a distinctly brown discoloration, do not use. Slight foaming of the product upon reconstitution is not unusual. After reconstitution, ILARIS should be kept from light, and can be kept at room temperature if used within 60 minutes of reconstitution.

92. Otherwise, it should be refrigerated at 2° C. to 8° C. (36° F. to 46° F.) and used within 4 hours of reconstitution. STEP 4: Using a sterile 1-mL syringe and needle, carefully withdraw the required volume depending on the dose to be administered and subcutaneously inject using a 27-gauge×0.5" needle. Injection into scar tissue should be avoided as this may result in insufficient exposure to ILARIS. Discard any unused product or waste material in accordance with local requirements.

(3) Administration

93 Canakinumab can be administered as a single subcutaneous injection of 150 mg in 1 mL total volume into abdomen or anterior thigh. The drug name, dose, and timing of this prophylactic medication can be recorded.

(4) Concomitant Medications

94. Concomitant medications are defined as drug or biological products other than the study drug(s) taken by a participant during the clinical trial. This includes other prescription medications (including preventive vaccines), over-the-counter medications, herbal medications, vitamins, and food supplements.

95. A comprehensive list of participant's concomitant medications can be collected at baseline and at each visit. This can include the name of the drug/vitamin/supplement, dose, route of administration, start and stop dates, and the reason for which the medication was taken. All medications can be listed by participant using the generic name(s) of the drug/vitamin/supplement.

96. Severe/Serious adverse events related to the use of a concomitant drug/vitamin/supplement can be documented on the appropriate AE CRF.

(5) Gout Flare Prophylaxis

97. Gout flare prophylaxis (in addition to study medication canakinumab) can be prescribed as deemed clinically indicated by the study physician.

(6) Gout Flare Treatment

98. An increase in gout flares is frequently observed upon initiation of anti-hyperuricemic therapy, including treatment with pegloticase. Participants are instructed to contact the site within 12 hours of the onset of symptoms. Gout flares can be confirmed through questioning or direct observation. All participants who experience a gout flare during the study are prescribed anti-inflammatory treatment (e.g., NSAIDs, colchicine, corticosteroids) as deemed clinically indicated by the study physician.

(7) Adverse Events (AE)

99. This is a Phase IV, open label trial examining canakinumab as prophylaxis to prevent gout flares when initiating treatment for uncontrolled gout with pegloticase in combination with methotrexate. All three medications are FDA approved and have been in clinical use for over 12 years, but are not commonly co-administered. An AE is defined as any untoward event whether or not considered related to the use of canakinumab. Any worsening (i.e. any clinically significant adverse change in frequency or intensity) of a preexisting condition which is temporally associated with the use of canakinumab is also considered an AE. Abnormal laboratory values or test results constitute AEs only if they induce clinical signs or symptoms or require therapy, and are recorded on the AE CRF under the signs, symptoms or are associated with diagnoses associated with them.

100. Screening conditions are not be considered AE; however, worsening of a preexisting condition can be considered an AE. The start for collecting AEs is at our baseline, Visit 1. We can report all severe/serious AEs according to appropriate authority (e.g., FDA, IRB) in compliance with guidelines and regulations.

(a) Infusion Reactions (IRs)

(i) IR Definition

An IR can be defined as any infusion-related AE or cluster of temporally related AEs, not attributable to another cause, which occur during or within 2 hours after the infusion of pegloticase. Other AEs that occur outside of the 2-hour window following the infusion may also be categorized as an IR per site PI discretion. Signs and symptoms of the IR, and treatments administered, are documented in the medical record and in the CRF. Examples of AEs not considered possible IRs include but are not limited to: laboratory abnormalities that are unlikely to have occurred during or within 2 hours following the infusion (e.g., anemia, hypercholesterolemia), gout flares, most infectious diseases, or the recurrence or worsening of a known chronic medical problem identified in the participant's medical history.

(ii) IR Prophylaxis

IRs are not uncommon when biological agents are administered by IV infusion. Therefore, all participants may receive at the discretion of the PI pre-treatment prophylaxis which may include antihistamine and corticosteroid prior to each infusion of pegloticase as per the Krystexxa package insert. The name, dose, route, date, and time of administration of each prophylactic medication are recorded in the medical record and in the CRF.

3. Example 3: Canakinumab (Ilaris) Prophylaxis without Corticosteroids, Prevented Flares in Patients Initiating Pegloticase (KRYSTEXXA®) with Methotrexate for Uncontrolled Gout: a Prospective 101. Pegloticase+methotrexate (MTX), FDA approval July 2022, is effective at reducing signs/symptoms of uncontrolled gout. The pivotal trial (MIRROR RCT) confirmed pegloticase+MTX superiority in safety and efficacy (mo 6 response rate: 71% vs. 39%; IR rate: 4% vs. 31%). Gout flare, the most common adverse event, occurred in 54% of patients in the pegloticase+MTX treatment group despite prophylaxis with daily NSAIDs or colchicine and pre-infusion IV methylprednisone 125 mg. Canakinumab is FDA approved for treatment of recurrent gout flares in patients who cannot be treated with NSAIDs, colchicine, or repeated courses of corticosteroids (CS) and can reduce subsequent flares during allopurinol initiation, presumably through the IL-1 pathway, but has not been studied as prophylaxis. We report results of canakinumab prophylaxis (without CS, NSAIDs, or colchicine) to prevent gout flares associated with initiating pegloticase+MTX (MIRROR-C).

a) Methods:

102. Twelve sequential adult uncontrolled gout patients scheduled to initiate pegloticase+MTX treatment were consented. Patients were TB negative within 6 mos and able to take MTX for ≥4 wks prior to pegloticase initiation. Key exclusion criteria (similar to MIRROR RCT) included MTX or pegloticase contraindication, previous uricase exposure, eGFR <25 mL/min/1.73 m 2 or dialysis. Canakinumab 150 mg was given subcutaneously 7 days prior to the first pegloticase infusion and ≥3 wks since starting MTX. Pegloticase every 2 wks+MTX was initiated without preinfusion CS, NSAIDs, or colchicine. Assessment for gout flares using validated, patient reported criteria published by Gaffo et al[7] was performed at canakinumab injection and every 2 wks at each pegloticase infusion (or appointment if pegloticase was discontinued) for 6 mos. The primary endpoint was monthly gout flares vs. previously published results from MIRROR RCT, with particular interest at 12 wks. Preinfusion serum uric acid (SUA) and pegloticase response rates were also collected.

b) Results

103. Twelve patients met inclusion criteria from 3 separate sites and 11 received canakinumab prophylaxis and ≥1 pegloticase infusion. One patient was lost to follow up after infusion 1. Two patients discontinued pegloticase, 1 due to a rise in SUA and 1 by patient choice. One patient experienced a rise in SUA but continued pegloticase. No new gout flares were reported in any patient receiving canakinumab prophylaxis and all active gout flares resolved within 48 hours of administration (FIG. 1). Overall pegloticase+MTX response rate was comparable to previous MIRROR RCT results with no new safety signals.

c) Discussion

104. Prophylaxis using a single dose of canakinumab 150 mg prevented gout flares in all patients initiating pegloticase+MTX for uncontrolled gout without CS and did not compromise efficacy or safety. Although additional studies would be needed to corroborate these results, this data supports prophylaxis with canakinumab instead of CS when initiating pegloticase+MTX treatment.

D. References

Administration Food and Drug.AAC Briefing Document Krystexxa (Pegloticase).2009. Mar. 23, 2016

Albert J A, Hosey T, LaMoreaux B. Increased efficacy and tolerability of pegloticase in patients with uncontrolled gout co-treated with methotrexate: a retrospective study. Rheumatol Ther. 2020; 7:639-48.

Baraf H. S., Matsumoto A. K., Maroli A. N., Waltrip R. W., 2nd. Resolution of gouty tophi after twelve weeks of pegloticase treatment. Arthritis Rheum. 2008; 58(11): 3632-4.

Baraf H S, Yood R A, Ottery F D, Sundy J S, Becker M A. Infusion-related reactions with pegloticase, a recombinant uricase for the treatment of chronic gout refractory to conventional therapy. J Clin Rheumatol. 2014; 20:427-32.

Becker M A, Schumacher H R, Benjamin K L, Gorevic P, Greenwald M, Fessel J, et al. Quality of life and disability in patients with treatment-failure gout. J Rheumatol. 2009; 36:1041-8.

Botson J K, Peterson J. Pretreatment and coadministration with methotrexate improved durability of pegloticase response: an observational, proof-of-concept case series. J Clin Rheum. 2022; 28(1):e129-34.

Botson J K, Tesser J R P, Bennett R, Kenney H M, Obermeyer K O, LaMoreaux B, et al. Pegloticase in combination with methotrexate in patients with uncontrolled gout: a multicenter, open-label study (MIRROR). J Rheumatol. 2021; 48:767-74.

Botson, J K et al. (2023) Arthritis Rheumatol 75(2):293-304

Brook R A, Forsythe A, Smeeding J E, Lawrence Edwards N. Chronic gout. epidemiology, disease progression, treatment and disease burden. Curr Med Res Opin. 2010; 26:2813-21.

Chen J H, Lan J L, Cheng C F, Liang W M, Lin H Y, Tsay G J, et al. Effect of urate-lowering therapy on all-cause and cardiovascular mortality in hyperuricemic patients without gout. A case-matched cohort study PloS One. 2015; 10:e0145193.

Choi H K, Curhan G. Independent impact of gout on mortality and risk for coronary heart disease. Circulation. 2007; 116:894-900.

Choi H K, Ford E S, Li C, Curhan G. Prevalence of the metabolic syndrome in patients with gout: the third national health and nutrition examination survey. Arthritis Care Res (Hoboken). 2007; 57:109-15.

Cimzia (certolizumab pegol) [package insert]. Smyrna: UCB, Inc.; 2016.

Copur S, Demiray A, Kanbay M. Uric acid in metabolic syndrome: does uric acid have a definitive role? Eur J Intern Med. 2022; 50953-6205(22):00165-0 (Epub ahead of print).

Culleton B F, Larson M G, Kannel W B, Levy D. Serum uric acid and risk for cardiovascular disease and death: the Framingham Heart Study. Ann Intern Med. 1999; 131:7-13.

Dalbeth N, Nicolaou S, Baumgartner S, Hu J, Fung M, Choi H K. Presence of monosodium urate crystal deposition by dual-energy CT in patients with gout treated with allopurinol. Ann Rheum Dis. 2018; 77:364-70.

Dervieux T, Orentas Lein D, Marcelletti J, Pischel K, Smith K, Walsh M, Richerson R. HPLC determination of erthrocyte methotrexate polyglutamates after low-dose methotrexate therapy in patients with rheumatoid arthritis. Clin Chem. 2003; 49:1632-41.

Fels E, Sundy J S. Refractory gout: what is it and what to do about it? Current Opin Rheumatol. 2008; 20:198-202.

FitzGerald J D, Dalbeth N, Mikuls T, Brignardello-Petersen R, Guyatt G, Abeles A M, et al. 2020 american college of rheumatology guideline for the management of gout. Arthritis Care Res (Hoboken). 2020; 72:744-60.

Food and Drug Administration Arthritis Advisory Committee.KRYSTEXXA™ (pegloticase) for intravenous infusion BLA No. 125293 2009.

Gaffo A L, Schumacher H R, Saag K G, Taylor W J, Dinnella J, Outman R, et al. Developing a provisional definition of flare in patients with established gout. Arthritis Rheum. 2012; 64:1508-17.

Gaffo, A L et al. (2018) Arthritis Rheumatol 70(3):462-467

Harrold L R, Andrade S E, Briesacher B A, Raebel M A, Fouayzi H, Yood R A, Ockene I S. Adherence with urate-lowering therapies for the treatment of gout. Arthritis Res Ther. 2009; 11(2):R46.

Hershfield M S, Ganson N J, Kelly S J, Scarlett E L, Jaggers D A, Sundy J S. Induced and pre-existing anti-polyethylene glycol antibody in a trial of every 3-week dosing of pegloticase for refractory gout, including in organ transplant recipients. Arthritis Res Ther. 2014; 16:R63.

Horizon Therapeutics. News release Jul. 8, 2022.

Humira (adalimumab) [package insert]. North Chicago: AbbVie Inc.; 2021.

Keenan R T, Baraf H S B, LaMoreaux B. Use of pre-infusion serum uric acid levels as a biomarker for infusion reaction risk in patients on pegloticase. Rheumatol Ther. 2019; 6:299-304.

Khanna P, Khanna D, Cutter G, Foster J, Melnick J, Jaafar S, et al. Reducing immunogenicity of pegloticase with concomitant use of mycophenolate mofetil in patients with refractory gout: a phase II, randomized, double-blind, placebo-controlled trial. Arthritis Rheumatol. 2021; 73(8):1523-32 (Epub ahead of print).

Khanna P., Khanna D., Storgard C., Baumgartner S., Morlock R. A world of hurt: failure to achieve treatment goals in patients with gout requires a paradigm shift. Postgrad Med. 2016; 128(1):34-40

Kim S Y, Guevara J P, Kim K M, Choi H K, Heitjan D F, Albert D A. Hyperuricemia and risk of stroke: a systematic review and meta-analysis. Arthritis Rheum. 2009; 61:885-92.

Kingsbury S R, Conaghan P G, McDermott M F. The role of the NLRP3 inflammasome in gout. J Inflamm Res. 2011; 4:39-49.

LaMoreaux B, Francis-Sedlak M, Svensson K, Holt R Immunomodulation co-therapy with pegloticase: database trends 2014-2019 [abstract]. Ann Rheum Dis. 2020; 79(suppl 1):108.

Lipsky P E, Calabrese L H, Kavanaugh A, Sundy J S, Wright D, Wolfson M, et al. Pegloticase immunogenicity: the relationship between efficacy and antibody development in patients treated for refractory chronic gout. Arthritis Res Ther. 2014; 16:R60.

Maini R N, Breedveld F C, Kalden J R, Smolen J S, Davis D, Macfarlane J D, et al. Therapeutic efficacy of multiple intravenous infusions of anti-tumor necrosis factor alpha monoclonal antibody combined with low-dose weekly methotrexate in rheumatoid arthritis. Arthritis Rheum. 1998; 41:1552-63.

Masri K, Winterling K, LaMoreaux B. Leflunomide co-therapy with pegloticase in uncontrolled gout. Ann Rheum Dis. 2020; 79:450.

Mikuls T. R., Farrar J. T., Bilker W. B., Fernandes S., Schumacher H. R., Jr., Saag K. G. Gout epidemiology: results from the UK General Practice Research Database, 1990-1999. Ann Rheum Dis. 2005; 64(2):267-72

Nozue T, Yamamoto S, Tohyama S, Fukui K, Umezawa S, Onishi Y, et al. Correlations between serum uric acid and coronary atherosclerosis before and during statin therapy. Coron Art Dis. 2014; 25:343-8.

Pan A, Teng G G, Yuan J M, Koh W P. Bidirectional association between self-reported hypertension and gout: the Singapore Chinese Health Study. PLoS ONE. 2015; 10:e0141749.

Pan A, Teng G G, Yuan J M, Koh W P. Bidirectional association between diabetes and gout: the Singapore Chinese Health Study. Sci Rep. 2016; 6:25766.

Park J J, Roudier M P, Soman D, Mokadam N A, Simkin P A. Prevalence of birefringent crystals in cardiac and prostatic tissues, an observational study. BMJ Open. 2014; 4:e005308.

Rainey H, Baraf H S B, Yeo A, Lipsky P. Companion immunosuppression with azathioprine increases the frequency of persistent responsiveness to pegloticase in patients with chronic refractory gout. Ann Rheum Dis. 2020; 79:438.

Richette P, Doherty M, Pascual E, Barskova V, Becce F, Castaneda-Sanabria J, et al. 2016 updated EULAR evidence-based recommendations for the management of gout. Ann Rheum Dis. 2017; 76:29-42.

Riedel A A, Nelson M, Joseph-Ridge N, Wallace K, MacDonald P, Becker M. Compliance with allopurinol therapy among managed care enrollees with gout: a retrospective analysis of administrative claims. J Rheumatol. 2004; 31:1575-81.

Roddy Edward, Doherty Michael. Gout. Epidemiology of gout. Arthritis Research & Therapy. 2010; 12(6):

Roughley M J, Belcher J, Mallen C D, Roddy E. Gout and risk of chronic kidney disease and nephrolithiasis: meta-analysis of observational studies. Arthritis Res Ther. 2015; 17:90.

Saag K. G., Choi H. Epidemiology, risk factors, and lifestyle modifications for gout. Arthritis Res Ther. 2006; 8 Suppl 1:S2

Sattui S. E., Singh J. A., Gaffo A. L. Comorbidities in patients with crystal diseases and hyperuricemia. Rheum Dis Clin North Am. 2014; 40(2):251-78

Schlesinger, N et al. (2011) Ann Rheum Dis 70(7):1264-71

Singh J. A., Strand V. Gout is associated with more comorbidities, poorer health-related quality of life and higher healthcare utilisation in US veterans. Ann Rheum Dis. 2008; 67(9):1310-6

Sundy J S, Baraf H S, Yood R A, Edwards N L, Gutierrez-Urena S R, Treadwell E L, et al. Efficacy and tolerability of pegloticase for the treatment of chronic gout in patients refractory to conventional treatment: two randomized controlled trials. JAMA. 2011; 306:711-20.

Sundy, J S et al. (2008) Arthritis Rheum 58(9):2882-91

Tamariz L, Hernandez F, Bush A, Palacio A, Hare J M. Association between serum uric acid and atrial fibrillation: a systematic review and meta-analysis. Heart Rhythm. 2014; 11:1102-8.

Weisman M H, Moreland L W, Furst D E, Weinblatt M E, Keystone E C, Paulus H E, et al. Efficacy, pharmacokinetic, and safety assessment of adalimumab, a fully human anti-tumor necrosis factor-alpha monoclonal antibody, in adults with rheumatoid arthritis receiving concomitant methotrexate: a pilot study. Clin Ther. 2003; 25:1700-21.

Wertheimer Albert, Morlock Robert, Becker Michael A. A Revised Estimate of the Burden of Illness of Gout. Current Therapeutic Research. 2013; 75:1-4

Woodworth T, Furst D E, Alten R, Bingham C O 3rd, Yocum D, Sloan V, et al. Standardizing assessment and reporting of adverse effects in rheumatology clinical trials II: the rheumatology common toxicity criteria v.2.0. J Rheumatol. 2007; 34:1401-14.

Yu K H, Kuo C F, Luo S F, See L C, Chou I J, Chang H C, et al. Risk of end-stage renal disease associated with gout: a nationwide population study. Arthritis Res Ther. 2012; 14:R83.

Zhao G, Huang L, Song M, Song Y. Baseline serum uric acid level as a predictor of cardiovascular disease related mortality and all-cause mortality: a meta-analysis of prospective studies. Atherosclerosis. 2013; 231:61-8.

Zhu Y., Pandya B. J., Choi H. K. Prevalence of gout and hyperuricemia in the US general population: the National Health and Nutrition Examination Survey 2007-2008. Arthritis Rheum. 2011; 63(10):3136-41

What is claimed is:

1. A method of inhibiting gout flares in a patient receiving gout treatment, comprising prior to the occurrence of gout flares administering a gout flare-ameliorating amount of at least one IL-1β inhibitor, at least one immunomodulatory agent, and at least one uricase; wherein at least one dose of the IL-1β inhibitor is administered either alone or in combination with the immunomodulatory agent prior to or concurrent with administration of the uricase; and wherein the uricase is administered alone or in combination with the immunomodulatory agent; wherein the at least one IL-1β inhibitor is selected from the group consisting of canakinumab, anakinra, gevokizumab, and rilonacept; and wherein the immunomodulatory agent is selected from the group consisting of methotrexate, mycophenolate, azathioprine, leflunomide, pomalidomide, lenalidomide, sulfasalazine diphenhydramine, cetirizine, famotidine, montelukast, acetaminophen, methylprednisolone, folic acid, and prednisone.

2. The method of claim 1, wherein the at least one IL-1β inhibitor is administered prior to, simultaneously to, or contemporaneously with administration of the immunomodulatory agent.

3. The method of claim 1, wherein the at least one IL-1β inhibitor is administered subsequent to administration of the immunomodulatory agent.

4. The method of claim 3, wherein the at least one IL-1β inhibitor is administered three weeks after administration of the immunomodulatory agent.

5. The method of claim 1, wherein the immunomodulatory agent comprises methotrexate or mycophenolate.

6. The method of claim 1, wherein the IL-1β inhibitor is administered concurrently with the uricase.

7. The method of claim 1, wherein the IL-1β inhibitor is administered at least one to seven days before administration of the uricase.

8. The method of claim 1 wherein the uricase comprises pegloticase or rasburicase.

9. The method of claim 1, wherein the IL-1β inhibitor comprises canakinumab.

10. The method of claim 1, wherein the method does not include the administration of a corticosteroid.

11. The method of claim 1, wherein the immunomodulatory agent is administered weekly for at least three weeks; wherein the IL-1β inhibitor is administered once; and wherein the uricase is administered bi-weekly.

12. The method of claim 11, wherein the first administration of the immunomodulatory agent occurs before administration of the IL-1β inhibitor.

13. The method of claim 12, wherein administration of the IL-1β inhibitor occurs three weeks after the first administration of the immunomodulatory agent.

14. The method of claim 12, wherein the immunomodulatory agent continues to be administered weekly after administration of the IL-1β inhibitor.

15. The method of claim 11, wherein the first administration of the immunomodulatory agent occurs after administration of the IL-1β inhibitor.

16. The method of claim 1, wherein the immunomodulatory agent is administered for at least 4 weeks prior to administration of the uricase; wherein the at least one dose of an IL-1β inhibitor is administered either alone or in combination with the immunomodulatory agent three weeks after first administration of the immunomodulatory agent and seven days before administration of the uricase.

17. A treatment regimen for inhibiting gout flares in a patient in need thereof, comprising:

a) administering an immunomodulatory agent; wherein the immunomodulatory agent is selected from the group consisting of methotrexate, mycophenolate, azathioprine, leflunomide, pomalidomide, lenalidomide, sulfasalazine diphenhydramine, cetirizine, famotidine, montelukast, acetaminophen, methylprednisolone, folic acid, and prednisone;

b) administering at least one dose of an IL-1β inhibitor; wherein the at least one IL-1β inhibitor is selected from the group consisting of canakinumab, anakinra, gevokizumab, and rilonacept; and c) administering a uricase, wherein at least one dose of an IL-1β inhibitor is administered either alone or in combination with the immunomodulatory agent; and wherein the uricase is administered for a period of time to control gout; and wherein the IL-1β inhibitor is administered prior to or concurrent with the first administration of the uricase.

18. The treatment regimen of claim 17, wherein: immunomodulatory agent is administered weekly for at least three weeks, the IL-1β inhibitor is administered once, and the uricase is administered for at least bi-weekly.

19. The treatment regimen of claim 17, wherein the first administration of the immunomodulatory agent occurs before administration of the IL-1β inhibitor.

20. The treatment regimen of claim 19, wherein the IL-1β inhibitor is administered three weeks after the first administration of the immunomodulatory agent.

21. The treatment regimen of claim 19, wherein the immunomodulatory agent continues to be administered weekly after administration of the IL-1β inhibitor.

22. The treatment regimen of claim 17, wherein the first administration of the immunomodulatory agent occurs after administration of the IL-1β inhibitor.

23. The treatment regimen of claim 17, wherein the IL-1β inhibitor is administered at least one to seven days before the first administration of the uricase.

24. The treatment regimen of claim 17, wherein the immunomodulatory agent comprises methotrexate or mycophenolate.

25. The treatment regimen of claim 17, wherein the IL-1β inhibitor comprises canakinumab.

26. The treatment regimen of claim 17, wherein the uricase comprises pegloticase or rasburicase.

27. The treatment regimen of claim 17, wherein method does not comprise the administration of a corticosteroid.

* * * * *

SEQUENCE LISTING

```
Sequence total quantity: 1
SEQ ID NO: 1            moltype = AA  length = 298
FEATURE                 Location/Qualifiers
source                  1..298
                        mol_type = protein
                        organism = synthetic construct
SEQUENCE: 1
TYKKNDEVEF VRTGYGKDMI KVLHIQRDGK YHSIKEVATT VQLTLSSKKD YLHGDNSDVI  60
PTDTIKNTVN VLAKFKGIKS IETFAVTICE HFLSSFKHVI RAQVYVEEVP WKRFEKNGVK  120
HVHAFIYTPT GTHFCEVEQI RNGPPVIHSG IKDLKVLKTT QSGFEGFIKD QFTTLPEVKD  180
RCFATQVYCK WRYHQGRDVD FEATWDTVRS IVLQKFAGPY DKGEYSPSVQ KTLYDIQVLT  240
LGQVPEIEDM EISLPNIHYL NIDMSKMGLI NKEEVLLPLD NPYGKITGTV KRKLSSRL    298
```